(12) United States Patent
Viltchinskaia et al.

(10) Patent No.: US 7,897,032 B2
(45) Date of Patent: Mar. 1, 2011

(54) METHOD AND APPARATUS FOR STRIPPING VOLTAMMETRIC AND POTENTIOMETRIC DETECTION AND MEASUREMENT OF CONTAMINATION IN LIQUIDS

(76) Inventors: Elena Viltchinskaia, Roswell, NM (US); Peter A. Withers, Sandia Park, NM (US)

( * ) Notice: Subject to any disclaimer, the term of this patent is extended or adjusted under 35 U.S.C. 154(b) by 915 days.

(21) Appl. No.: 11/754,620

(22) Filed: May 29, 2007

(65) Prior Publication Data

US 2007/0278096 A1 Dec. 6, 2007

Related U.S. Application Data

(63) Continuation-in-part of application No. 10/125,822, filed on Apr. 19, 2002, now abandoned.

(60) Provisional application No. 60/299,514, filed on Jun. 19, 2001.

(51) Int. Cl.
*G01N 27/26* (2006.01)

(52) U.S. Cl. ............... 205/790; 205/789; 205/789.5; 204/409; 204/434; 702/22; 702/23; 702/25; 422/68.1; 422/82.01; 422/82.02

(58) Field of Classification Search ............... 204/434, 204/409; 205/790, 789, 789.5; 702/22, 23, 702/25; 422/68.1, 82.01, 82.02
See application file for complete search history.

(56) References Cited

U.S. PATENT DOCUMENTS 5,391,270 A * 2/1995 Gui et al. ............... 205/789.5

* cited by examiner

*Primary Examiner* — Bruce F Bell
(74) *Attorney, Agent, or Firm* — Perman & Green LLP

(57) ABSTRACT

A sampling system for measuring the presence and concentration of inorganic ion species, including, metals, metalloids and non-metals, in a liquid solution including a first sampling unit. The first sampling unit includes a potentiometric subsystem configured to gather environmental metrics of the liquid sample, a preparation subsystem, coupled to the potentiometric module, the preparation subsystem being configured to prepare and isolate contaminants of concern in a flow of a liquid sample into metal, metalloid, or non-metal ionic forms; and a voltammetric subsystem selectively coupled to the preparation subsystem, potentiometric subsystem and a sample source, the voltammetric subsystem being configured to identify and determine a concentration of metal, metalloid, or non-metal ionic species through stripping voltammetry. The system is configured to compare a value of a stripping signal of the sample with a predetermined value to determine if dilution of the sample is required.

12 Claims, 14 Drawing Sheets

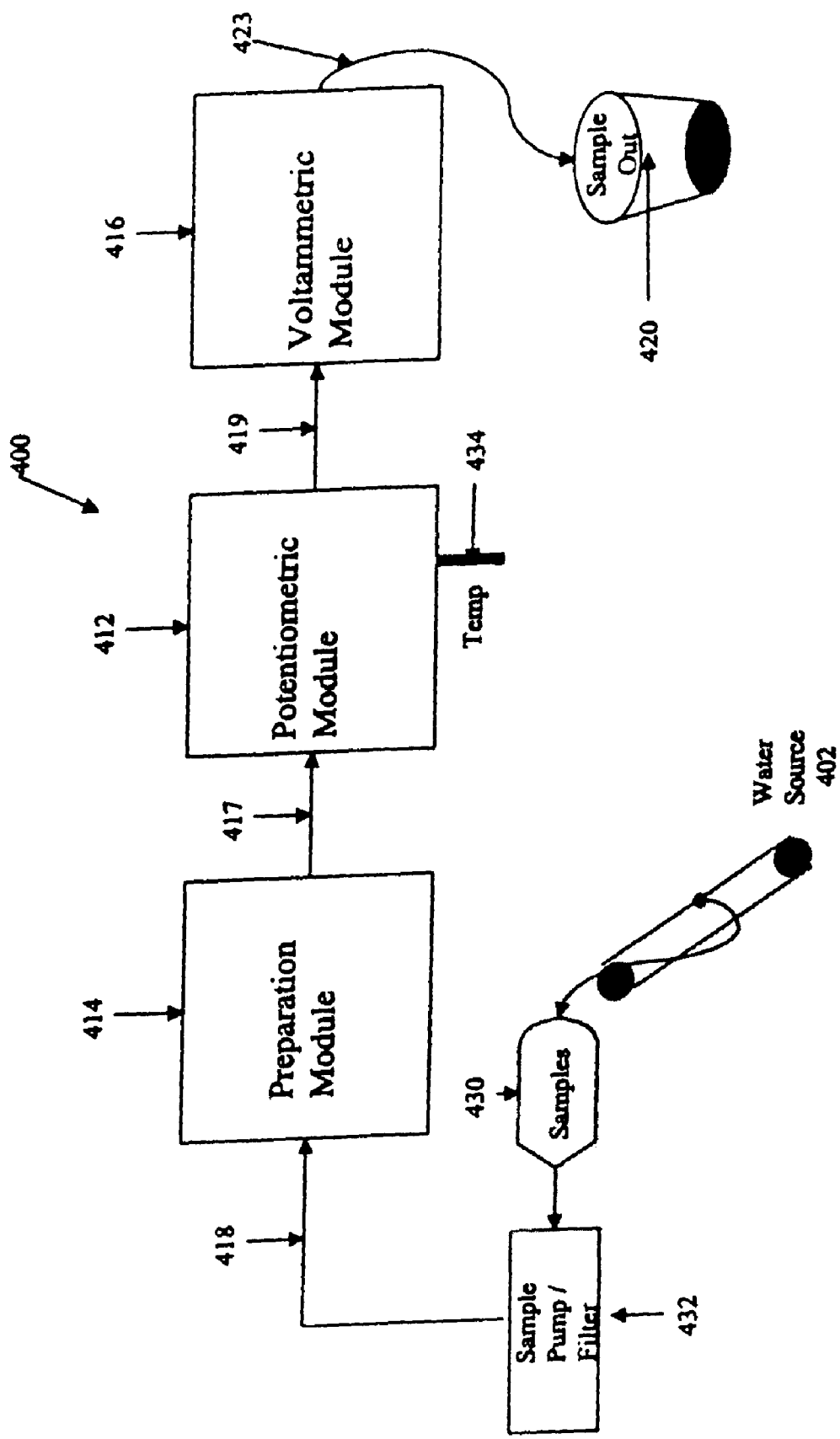

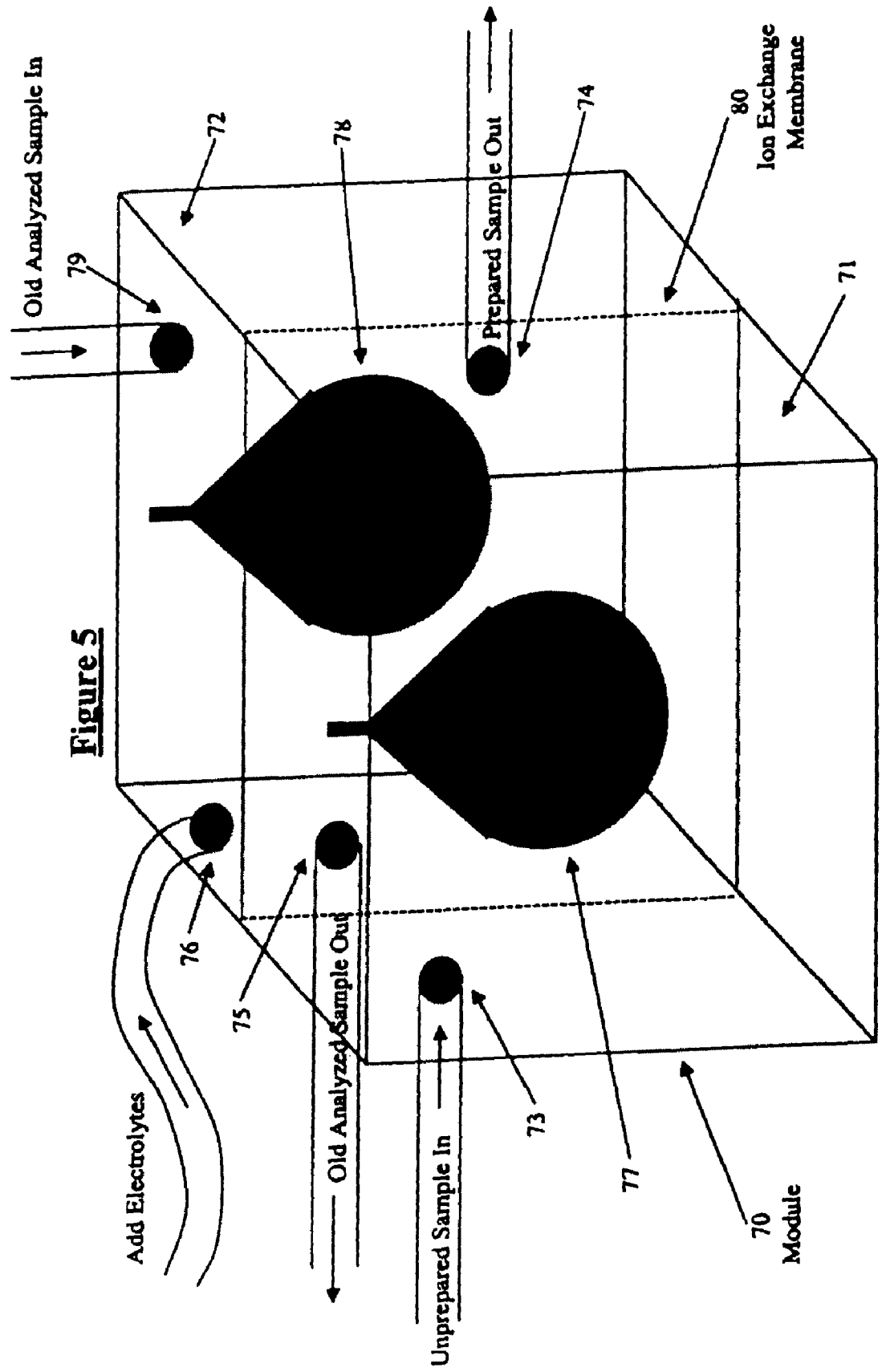

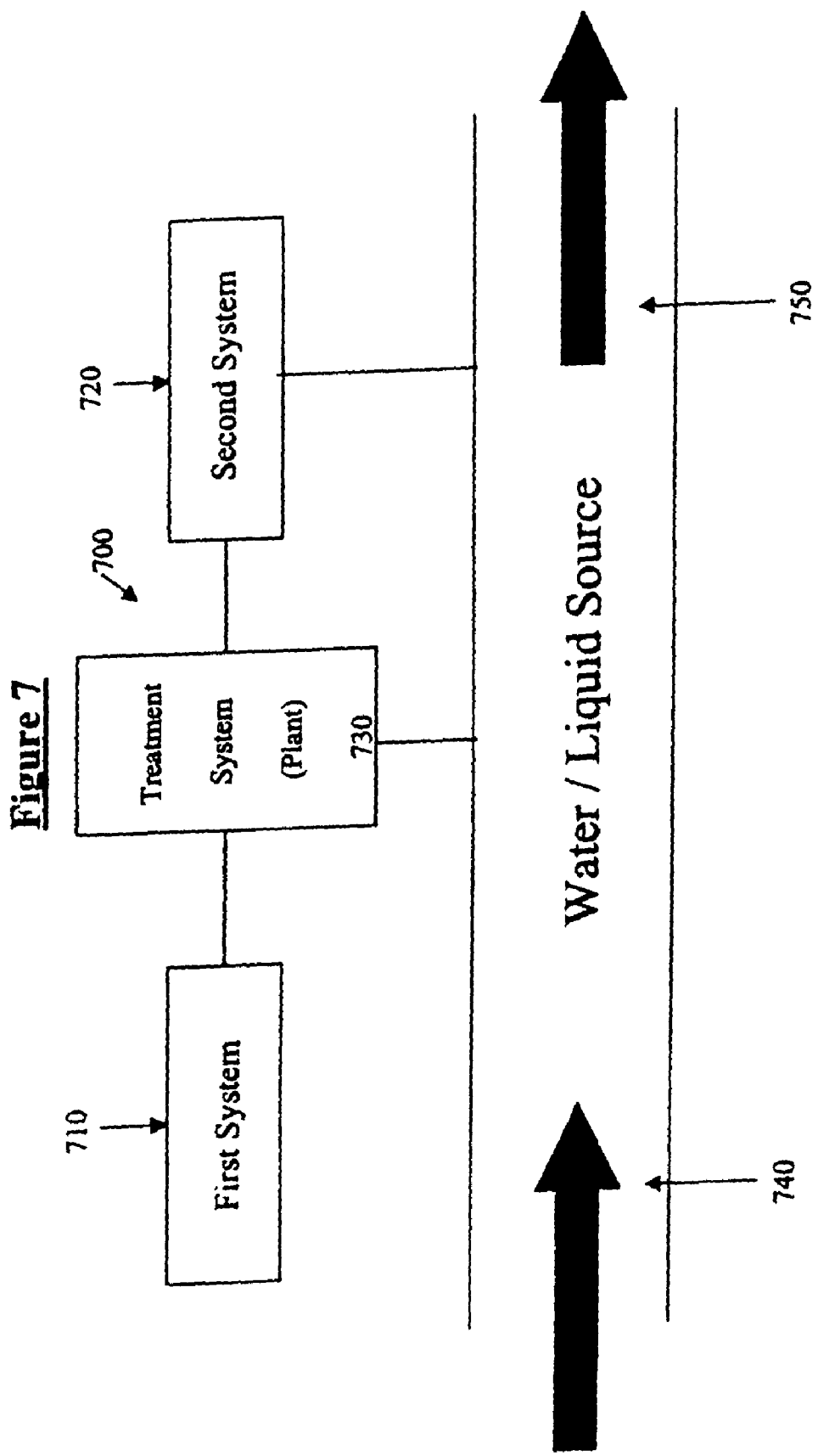

FIG. 11
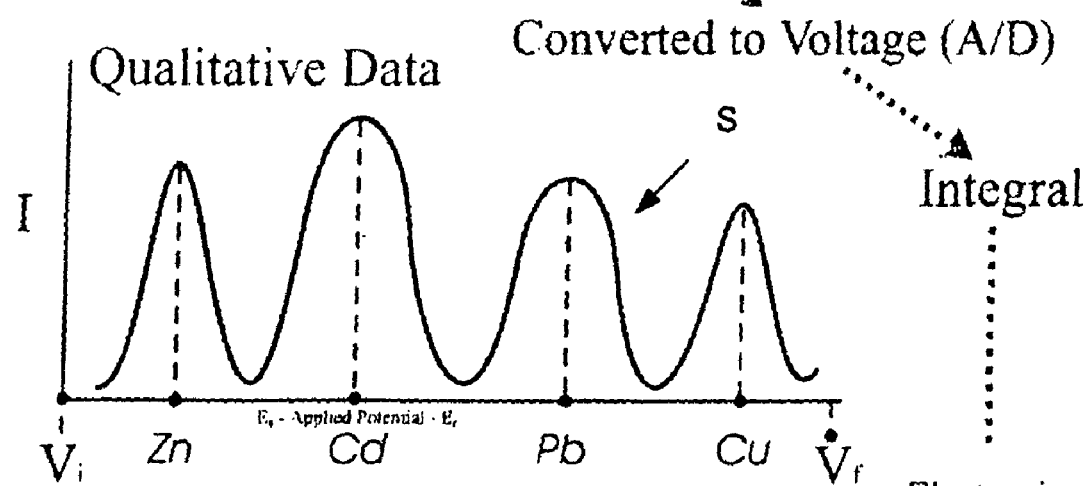
Vi = initial applied voltage
Vf = final applied voltage
FIG. 12
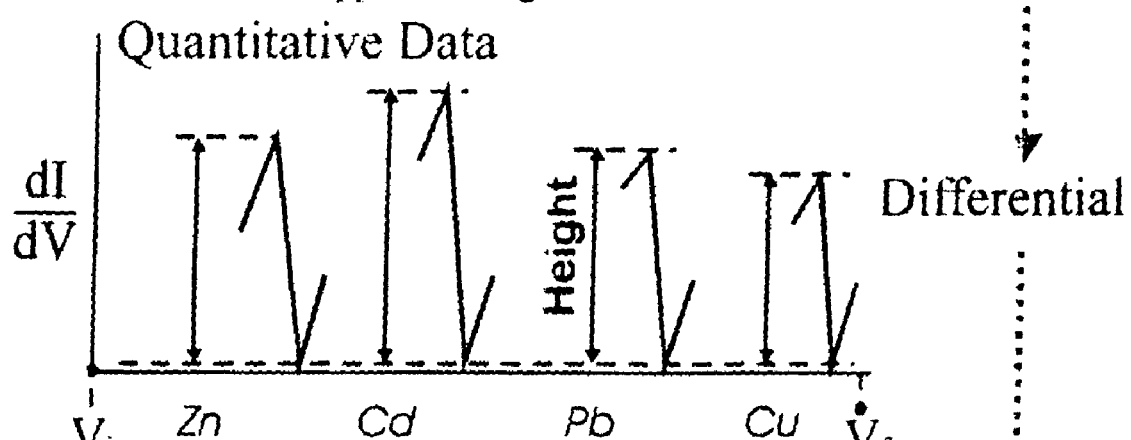
FIG. 13

METHOD AND APPARATUS FOR STRIPPING VOLTAMMETRIC AND POTENTIOMETRIC DETECTION AND MEASUREMENT OF CONTAMINATION IN LIQUIDS

CROSS-REFERENCE TO RELATED APPLICATIONS

This application is a continuation in part of application Ser. No. 10/125,822 entitled "METHOD AND APPARATUS FOR STRIPPING VOLTAMMETRIC AND POTENT IOMETRIC DETECTION AND MEASUREMENT OF CONTAMINATION IN LIQUIDS", filed on Apr. 19, 2002, now abandoned, which claims priority from U.S. Provisional Application No. 60/299,514, filed on Jun. 19, 2001.

BACKGROUND

1. Field

The exemplary embodiments generally relate to water processing and treatment, and more particularly, to the determination of electrochemically active ions in an aqueous solution.

2. Brief Description of Related Developments

In recent years there has been increasing demand for continuous real-time or near real-time monitoring of solution composition. Of particular interest are voltammetric detectors which measure the current response at given applied potential. Voltammetric detectors have applications which cover many fields and include for example environmental monitoring, process control, and biomedical monitoring. In particular, voltammetric detectors have found applications in heavy metal monitoring, clinical chemistry and as detectors for use in high-performance liquid chromatography HPLC.

Many other techniques are also currently available for the detection of contaminants. The development and improvement of these techniques has become a major focal point of analytical science because of the growing need to detect very small amounts of contaminants which adversely affect the environment. For example, mercury is regarded as a very toxic heavy metal, and its presence in soil and waterways represents a considerable health hazard. Government agencies throughout the world are increasing restrictions on the release of mercury to the environment. In some countries, a legislated limit of 2 parts-per-billion in drinking water has been enforced. Other potentially hazardous metals like lead and cadmium appear to be receiving the same scrutiny. The United States Environmental Protection Agency is lowering the allowable level of arsenic from 50 parts per billion down to 10 parts per billion or perhaps as low as 2 parts per billion in drinking water and in discharge permits.

The most commonly used methods for detecting various trace contaminants are atomic absorption (AA), inductively coupled plasma atomic emission (ICP-AE), and mass spectroscopy (MS). Each of these methods is suitable for trace analysis of nonmetals, metalloids, and metals, for example mercury in a laboratory setting. However, they often require well-controlled experimental conditions, expensive instrumentation, and frequent maintenance and calibration. Moreover, these methods usually require lengthy sample preparation, especially when other interfering elements or impurities are present in the sample under investigation. For these reasons, the methods mentioned above are not particularly well-suited for rapid analysis in the field or on-site in a treatment plant. Other methods which are sometimes suitable for contaminant detection and analysis in the field include X-Ray Fluorescence (XRF), colorimetry, and ion-selective electrodes (ISE). Special mention is made of XRF, which is used in the field because of its suitability for simultaneously detecting many contaminants without substantial sample preparation. However, the detection limits for this method (about 30-100 ppm) is not low enough for accurately determining very low levels of metals like mercury (2 ppb). Moreover, XRF is very dependent on the nature of the environmental sample. For example, if one is running a mercury analysis on both a soil sample and a plastic sample, a separate calibration curve must be prepared for each. Colorimetric techniques can be complicated and time-consuming. Also, such techniques are often very specific, e.g. selective to only one type of mercury complex, unlike the exemplary embodiment described herein, which are sensitive to all electro active species of an element.

One significant disadvantage of most commonly used methods in the detection of trace contaminants is the difficulty of performing analyses of highly complex samples, such as ocean water. In complex solutions there can be a wide variety of elements with concentration levels much higher than the contaminants of concern which often interfere with the accurate detection and quantification of trace elements. The concentration difference between the contaminants of concern and the other impurities in the water precludes the successful application of many analytical tools and techniques. The analysis of complex waters, such as ocean waters, by common methods requires the extraction of the contaminant of concern from the sample before an accurate analysis is made, e.g. in ocean water, one would have to separate the salts from the ions to be analyzed. One distinct advantage to the proposed voltammetric based system is that the effect of interference is minimized with comparatively little to no sample preparation required. Presently, many common methods frequently require extensive sample pretreatment to determine low impurity levels of highly complex samples. Consequently most analytical determinations are made off-line in a conventional laboratory setting.

Voltammetric detectors offer considerable advantages in terms of sensitivity and selectivity over other techniques mentioned above. Stripping Voltammetry (SV) techniques cathodic and also anodic, as well as potentiometric analysis (PA) have long been used in trace analysis. In stripping voltammetry, the electroactive species in the sample are first pre-concentrated on the working electrode surface using a controlled potential or potentials. Once the ions are electrochemically collected on the face of the working electrode, the potential is varied to strip the material from the electrode surface. The current used and produced while stripping the material from the electrode surface is proportional to the concentration of the electro-active species in the sample. Electrodes for SV comprise a working electrode, reference electrode (usually Ag/AgCl), and an auxiliary (counter) electrode, usually platinum or graphite. The system and process of the exemplary embodiments is designed to analyze samples with complex matrices, and the system is designed to eliminate any possible interferences.

Thus, prior art systems are mostly for laboratory use, labor intensive and require considerable supervision by skilled personnel in order to determine low levels of contaminant concentrations. Furthermore, conventional techniques are impaired by interference caused by high concentrations of other species present with the impurities. If interference is expected in conventional techniques, it is often necessary to alter the electrolyte by the addition of suitable substances to avoid interference.

U.S. Pat. No. 4,804,443, entitled, "METHOD AND APPARATUS FOR THE DETERMINATION OF ELECTRO- CHEMICALLY ACTIVE COMPONENTS IN A PROCESS STREAM", to Newman, et al., is effective in analysis of samples with high concentrations of impurities and high possibilities of interferences influence of sample matrix. The method comprises the steps of providing a sample in which the components are contained, and depositing the components onto a working electrode, altering the environment of the working electrode so that it is immersed in a supporting electrolyte by effecting a matrix exchange and stripping the deposited electrochemically active components from the working electrode into the supporting electrolyte. While this technique decreases interference problems, it significantly complicates the design of the system and algorithm of measurements. The method and apparatus utilize a mercury drop electrode, and the stability and size of the hanging mercury drop electrode are critical for overall accuracy and precision of the analysis. Also, additional steps of removing the sample from the cell after deposition of electrochemically active species and pumping electrolyte to the cell may cause unwanted changes on the electrode surface, which decreases the accuracy and precision of the analysis, thereby increasing the time of the analysis.

The system and process described in U.S. Pat. No. 4,626,992, entitled, "WATER QUALITY EARLY WARNING SYSTEM" to Greaves, et al., is confined to the detection and identification, via video monitoring techniques, of living organisms in sources of water supplies. The computer includes two software programs, one is responsive to the measurements by the sensors to derive a set of prediction parameters corresponding to the statistical distribution of the expected movement patterns of the organisms. The other software program is used for analyzing the organisms movement and comparing the observed movements with the set of prediction parameters, and for initiating the generation of the warning message when the organisms observed movements do not correspond to the prediction parameters.

U.S. Pat. No. 4,723,511, entitled, "CONTINUOUS MONITORING OF WATER QUALITY" to Solman, et al., describes a slow monitoring system for rapid feed forward and feedback data mechanism to manage a modern water treatment system. The purity and presence of contaminants is monitored by the reactions of a fish in a tank of water.

U.S. Pat. No. 5,646,863 Morton, entitled, "METHOD AND APPARATUS FOR DETECTING AND CLASSIFYING CONTAMINANTS IN WATER" describes a system which samples, detects, measures, and reports, in near-real time, the presence of contaminants and thereby provides users with the ability to continually monitor conformance of water with established health and safety standards. This apparatus has ample measurement sensors selected from group consisting of pH sensor, temperature sensor, metal sensor, organic sensor, radiation sensor and biosensor. Stripping electrochemical sensors for measuring metals in parts per billion concentrations is claimed. The system and process of the exemplary embodiments measures ions, elements and compounds of metals, nonmetals and metalloids. The Morton system determines the voltammetric analysis oxidation current, which is related to the concentration in a sample.

U.S. Pat. No. 4,300,909, entitled "PROCESS CONTROL" to Krumhansl, relates to methods and apparatus for measuring the chemical state of a fluid and physical state of both the fluid and an apparatus for treating it. It provides that information to an algorithm solving apparatus, and accomplishing process action in response to signals from the algorithm solving apparatus. Krumhansl is related to a swimming pool water treatment application. The process control includes functions of measuring the state of contaminants in a fluid and the interaction between the data and the apparatus for treating it by furnishing that information to an algorithm solving apparatus to accomplish functional responses.

U.S. Pat. No. 5,292,423 of Wang, entitled "METHOD AND APPARATUS FOR TRACE METAL TESTING" is limited to microliter samples measurements for metal concentration using mercury-coated screen printed electrodes. The exemplary embodiments measure a wide range of elements, metals, metalloids, and nonmetals and their derivatives, using different electrochemical methods, such as using ion-selective electrode and voltammetrically using solid state graphite electrodes.

U.S. Pat. No. 5,873,990 to Wojciechowski, entitled "HANDHELD ELECTROMONITOR DEVICE" the portable monitor is a microprocessor based instrument designed to conventionally and rapidly measure various analytes in environmental and biological samples. The system uses battery or DC power. Unique electronic, microchip configurations were developed for the device to make it portable, low-cost, safe and simple to operate the instrument. The instrument has a small size, and the analysis is done on a manually taken sample. Calibration of the device using calibration strips is proposed. The colloidal gold electrode is applied for electrochemical measurements. The device is developed for metal analysis.

SUMMARY

In one embodiment, a sampling system for measuring the presence and concentration of inorganic ion species, including, metals, metalloids and non-metals, in a liquid solution is provided. The sampling system includes a first sampling unit including a potentiometric subsystem configured to gather environmental metrics of the liquid sample, a preparation subsystem, coupled to the potentiometric module, the preparation subsystem being configured to prepare and isolate contaminants of concern in a flow of a liquid sample into metal, metalloid, or non-metal ionic forms; and a voltammetric subsystem selectively coupled to the preparation subsystem, potentiometric subsystem and a sample source, the voltammetric subsystem being configured to identify and determine a concentration of metal, metalloid, or non-metal ionic species through stripping voltammetry. The system is configured to compare a value of a stripping signal of the sample with a predetermined value to determine if dilution of the sample is required.

In another embodiment a method is provided. The method for detecting and identifying concentration levels of metal, metalloid, or non-metal ions includes measuring environmental metrics of a liquid sample, preparing and isolating contaminants of concern in a flow of a liquid sample into metal, metalloid, or non-metal ionic forms, identifying and determining a concentration of metal, metalloid, or non-metal ionic species through stripping voltammetry and comparing a value of a stripping signal of the sample with a predetermined value to determine if dilution of the sample is required.

In still another embodiment, a computer program product is provided. The computer program product includes a computer useable medium having computer readable code means embodied therein for causing a computer to measuring the presence and concentration of inorganic ion species, including, metals, metalloids and non-metals, in a liquid solution. The computer readable code means in the computer program product includes computer readable program code means for causing a computer to gather environmental metrics of the liquid sample, computer readable program code means for causing a computer to prepare and isolate contaminants of concern in a flow of a liquid sample into metal, metalloid, or non-metal ionic forms and computer readable program code means for causing a computer to identify and determine a concentration of metal, metalloid, or non-metal ionic species through stripping voltammetry, wherein a value of a stripping signal of the sample is compared with a predetermined value to determine if dilution of the sample is required.

BRIEF DESCRIPTION OF THE DRAWINGS

The foregoing aspects and other features of the exemplary embodiments are explained in the following description, taken in connection with the accompanying drawings, wherein:

FIG. 4 is a block diagram of one embodiment of a system incorporating features of an embodiment;

FIG. 5 is an exploded perspective view of one embodiment of a preparation module incorporating features of an embodiment;

FIG. 7 is block diagram of a water treatment system incorporating features of an embodiment;

FIG. 11 is a flow diagram in accordance with an embodiment; and

FIGS. 12-14 illustrate exemplary voltammograms in accordance with an embodiment.

DETAILED DESCRIPTION OF THE EXEMPLARY EMBODIMENT(s)

Figure 1:
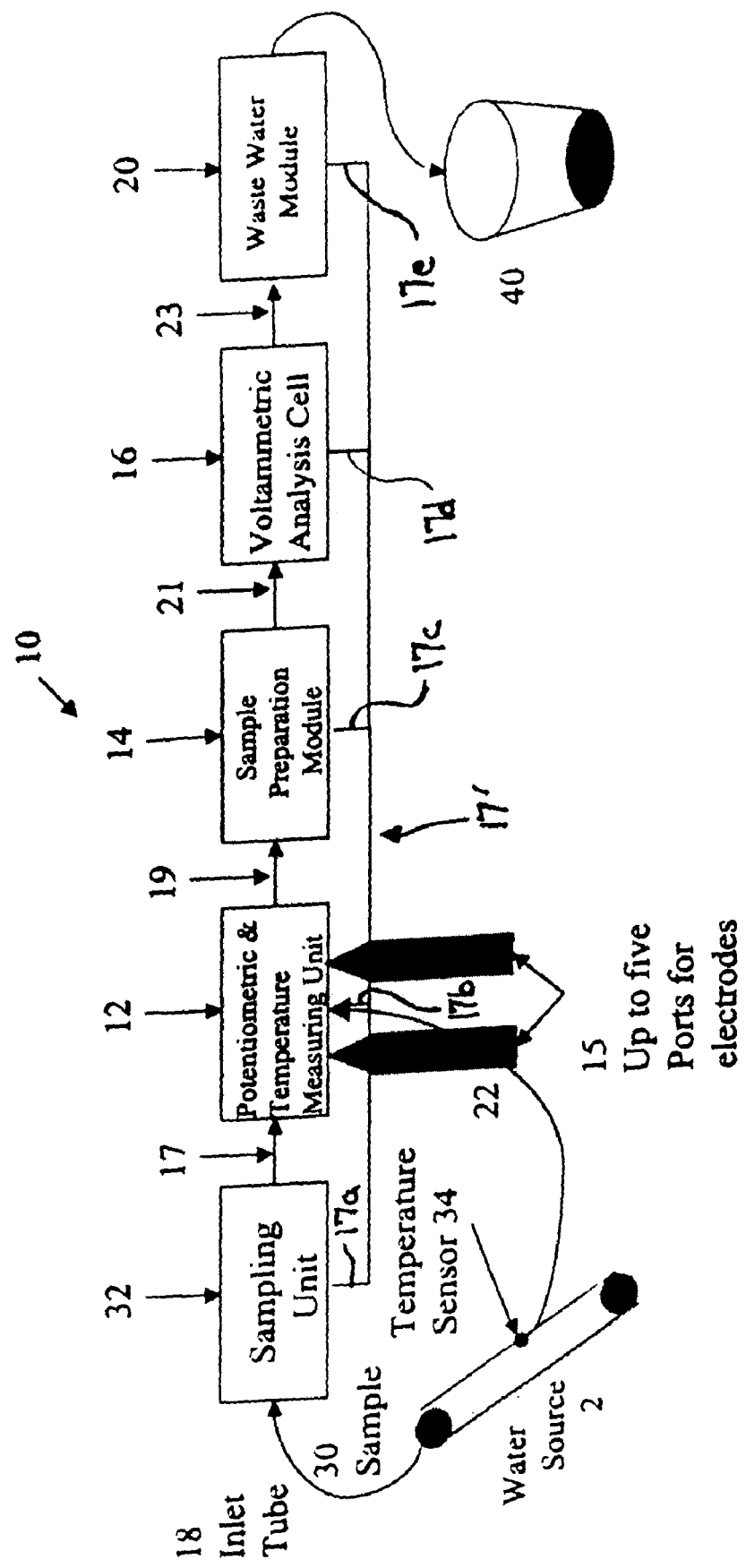
FIG. 1 is a block diagram of one embodiment of a system incorporating features of an embodiment.

Referring to FIG. 1, a block diagram of a system 10 incorporating features of the exemplary embodiments is shown. Although the exemplary embodiments will be described with reference to the embodiments shown in the drawings, it should be understood that the exemplary embodiments can be embodied in many alternate forms of embodiments. In addition, any suitable size, shape or type of elements or materials could be used.

The system 10 and process disclosed herein have a more innovative, capable and simple design. Different electrode types may be employed, e.g. gold plated electrode, in order to increase the sensitivity and selectivity of the analysis. The measurement cell design disclosed herein provides for significantly more stable electrodes that, when used with the proposed analysis technique will result in lower detection capability and faster analysis times which are critical to the on-line process control applications intended for this system.

The system 10 and process disclosed herein are designed to detect the presence and/or concentration of ions, compounds or elements other than living organisms in a solution. The system is designed to automatically identify, measure, calculate, and report the concentration of the contaminant species. Examples of contaminates include, but are not limited to beryllium, manganese, cobalt, nickel, copper, zinc, arsenic, selenium, silver, cadmium, antimony, mercury, lead and their derivatives. The methods of potentiometry and stripping voltammetry will be used for identifying and measuring the contaminant species; calculations will be accomplished with hardware and software, and the reporting will be done using the internal software. The method provides a highly objective and quantitative assessment of water characteristics from which to base early warning alarms from. The system and process provide fast quantitative on-line analysis using a highly accurate, automated, and sensitive Stripping Voltammetric technique that can be applied to, for example, samples taken from waste water, salt water and fresh water.

Although the concentration of the analyte in the continuously flowing fluid source (e.g. source 2 in FIG. 1) changes over time, at each point in time at which the sample 30 is taken the concentration of the analyte in that sample can be considered constant so that the system can measure the ion concentration at any given point in time. The system disclosed herein provides rapid updates on the changing characteristics of the solution being analyzed by providing rapid feedback to the operators of the system compared to the weekly or monthly sampling typical of conventional measurement systems.

The system 10 and process is configured to separately measure both oxidation and reduction current (i.e. the oxidation and reduction currents are not measured at the same time). The oxidation or reduction current is measured by taking derivatives of the oxidation or reduction currents. The oxidation and reduction currents and their derivatives are proportional to concentration of analyte in the sample. The system and process disclosed herein increases both the accuracy and precision of the analysis. The sample preparation procedure of Morton uses selective oxidizing or reducing of the sample in the presence of acid. In disclosed embodiments, the sample preparation procedure uses a universal approach to increase accuracy, selectivity and sensitivity of the analysis, that also includes the selective addition of organic or inorganic acid, base, salt, and chelating agents depending on the characteristics of the sample stream. Likewise each sample preparation procedure will be enhanced, if necessary, by cathodic or/and anodic treatment of sample with or without the addition of reagents depending on the requirements of the analysis. The purpose of the proposed sample preparation in Stripping Voltammetry technique is to convert the analyte to a specific electroactive form, and preparations may include, but are not limited to change of the oxidation state of the analyte, dissolving of the analyte, formation of new complex compounds with analyte, and oxidation of organic compounds, etc. Therefore, the exemplary embodiments have markedly improved the state of the art in Stripping voltammetry by lowering the detection limit from low ppb, to 5 ppt (parts per trillion), introducing a more selective sample preparation approach, and employing a more accurate analysis system of measuring derivatives of the oxidation or reduction current to determine the concentration of analyte in the sample. In addition the exemplary embodiments have significantly improved the integrated on-line process control capability described in Morton system, based on a flexible "feed forward" process control approach, the innovative software, and the alarm and system manipulation capabilities designed into the system, e.g. monitoring of water treatment system processes with the ability to notify plant personnel of alarm conditions as well as invoking system contingency operations such as the case of treatment malfunction, whereby the system of the exemplary embodiments will control the activation of valves and redirection of treatment effluent into holding tanks.

The disclosed system 10 and process incorporates both feed forward and feedback control signals to the process management system, as well as affecting a number of automatic electrical and mechanical responses, as it archives data for visual inspection and analysis.

The system 10 measures a wide range of elements, metals, metalloids, and nonmetals and their derivatives, using different electrochemical methods, such as using ion-selective electrode and voltammetrically using solid state graphite electrodes. Examples of ions that the system can measure include, but are not limited to, arsenic ions, mercury ions, copper ions, lead ions, cadmium ions, selenium ions, chloride ions, iodide ions, bromide ions and sulfide ions. The system 10 takes the integrated system analysis beyond the capability of the Wang system described above by automatically calculating concentrations and multiple water characteristics, preparation of reports, and managing outside pumps and valves.

The system 10 is designed for measurements in flow, the sample is automatically taken, automatically prepared, automatically reported to user(s), and the warning system is regularly integrated into a larger system to monitor contaminant values and regulate pumps and valves and alarm states. The system 10 generally may be part of a water treatment system comprising a first system 710 (FIG. 7) for measuring the presence and concentration of electro-active species in liquid solution in an upstream location from a water treatment process and a second system 720 (FIG. 7) for measuring the presence and concentration of electroactive species in a liquid solution in a downstream location from the water treatment process. The first and second systems may be adapted to communicate sample characteristics taken from the continuous flow of liquid to an independent treatment system adapted to control the treatment and processing of the contaminated water. Each of the systems 710, 720 comprises a highly advanced, sensitive, and responsive system of sensors and control hardware and software for the monitoring and control of contaminant flow through a treatment system.

As shown in FIG. 1, in one embodiment, the system 10 generally comprises a potentiometric module 12, a preparation module 14, and a voltammetric analysis module or cell 16. The preparation module 14 is adapted to convert a liquid sample into its electro-active form. The potentiometric module 12 may be coupled to the preparation module 14 and adapted to gather environmental metrics or characteristics of the liquid sample. The voltammetric module 16 is adapted to receive the sample from the potentiometric module 12 or preparation module 14 and identify and determine a concentration of electro-active species. The system 10 is generally adapted to continually draw samples 30 of fluid, such as for example water, from a source 2 and process it through the system 10 to measure the presence and concentrations of contaminant species in the sample. The system 10 takes sample after sample, so that as one sample is processed a new sample is taken. The system 10 can also include an automated hydraulic device for automatically drawing and conveying liquid samples and solutions through the system such as a sampling unit or pump 32 that is adapted to draw a sample 30 from a source 2 through an inlet tube or connection 18. In one embodiment the sampling unit 32 comprises an automated hydraulic device for automatically drawing and conveying liquid samples and solutions through the system. In alternate embodiments, any suitable device can be used for introducing the liquid sample into the processing system. A microprocessor based controller for the automated management of all operational aspects of the system, with the ability to network multiple individual sensor systems into a systems network capable of data sharing and archiving data may also be included in the water treatment system.

The liquid sample 30 can travel in between the various modules via for example, interconnecting hydraulic lines 17, 19, 21, and 23, and finally be discharged into the waste water module 20. As can also bee seen in FIG. 1, the system includes hydraulic line 17' which directly connects each of the sampling unit 32, potentiometric module 12, the preparation module 14, the voltammetric analysis module and waste water module 20 with each other via their respective connections 17a, 17b, 17c, 17d, and 17e. Hydraulic line 17' allows the voltammetric analysis module 12 to receive the sample directly from the sample unit 32, the potentiometric module 12 or the preparation module. The connections 17a-17e are configured to be opened and closed so that when one or more of the connections are opened the sample 30 flows into a respective module 12, 14, 16, 20. For example, hydraulic lines 17, 19, 21, 23 may also include valves so that when hydraulic line 19 is closed via its respective valve and connections 17b and 17d are opened the sample may flow directly from the potentiometric and temperature measuring unit 12 to the voltammetric analysis cell 16. In other embodiments the modules 32, 12, 14, 16 may be configured to redirect sample flow in the hydraulic lines 17, 19, 21, 23 and 17' without the use of separate valves. Pumps (not shown) can be used to move the fluid sample through the system. In alternate embodiments, the system 10 can include other such suitable components for rapidly and continuously conducting a variety of analyses on electroactive elements in aqueous solutions. It is a feature of the exemplary embodiments to integrate and manage data from electrochemical and ion selective analysis in an integrated treatment system and incorporate sensor data with electrical and mechanical interfaces to manage the contaminant flow in treatment processes. The disclosed embodiments generally comprise a fully automated analysis system, that will take a sample, analyze it by ion selective electrodes, prepare the sample for stripping voltammetric analysis, prepare the voltammetric sensor for analysis, analyze the sample, identify the contaminant species, calculate concentration levels, transfer results to the users and a system process controller, manage outside pumps or valves, and give warning signals.

As shown in FIGS. 1 and 4, a sample pump 32 and 432 will take a sample 30, 430 (aliquot) and deliver it to the potentiometric unit 12. Preferably, the sample pump 32 takes the sample or samples continuously (i.e. a new sample is taken after each time a previous sample is measured). The speed of flow may be varied in the range from 1 mL up to 50 mL per min. In one embodiment, the sampling unit 32 can include filters (not shown). The sample 30 can be filtered to protect the system 10 as required. The size and quantity of the filters in the sample pump 32 will vary depending on the purpose of the analysis. The speed of the sample intake may be varied, either automatically or manually.

The sample is transferred to the potentiometric module 12 for potentiometric analysis and temperature measurement of the sample (see FIG. 4 reference 434). A maximum of five measurements including potentiometric and ionic measurement of the aliquot can be conducted using a similar number of IEEE compatible commercially available potentiometric electrodes 15. As used herein the term "potentiometric electrodes" includes ion-selective electrodes. Examples of potentiometric sensors include, but are not limited to nitrate sensors, carbonate sensors and chloride sensors. The potentiometric module 12 (see FIG. 4 reference 412) can include at least one connectivity port for connecting remotely located measurement sensors such as a potentiometric electrode 34 for temperature measurement as can be seen in FIG. 1. For example, the potentiometric electrode 34 is inserted directly into the water source 2, which is located away from the potentiometric module 12. The remotely located potentiometric electrode may be configured to be in wired or wireless communication with the potentiometric module 12. The temperature of the initial sample can be measured in the source stream 2, using, for example, a commercially available thermistor 34, that will be connected to a temperature sensing device in the potentiometric unit 12 via a cable 22 or other suitable means. Different compositions of potentiommetric or ion-selective electrodes in the potentiometric module 12 may be selected, depending on the analysis requirements of the specific setup of the system. The different compositions of ion-selective electrodes are achieved through the interchangeability of ion-selective electrodes or sensors. The interchangeability of the electrodes allows for the measurement and analysis of different types of ions at the same time. In one example, each of the ion-selective electrodes in the potentiommetric module 12 can determine a respective type of ion. For example, the electrodes may be configured so that the combination of $Ca^{2+}$, $NO_3^-$, $F^-$, or $SO_4^{2-}$ ions can be measured and analyzed at the same time. In other embodiments, any combination of ion-selective electrodes can be employed. In an exemplary embodiment where the system 10 is computer controlled, all potentiometric and temperature measurements can be controlled by the "Parameters" window of the embedded software of the computer system.

The potentiometric module 12 is generally adapted to gather and evaluate environmental metrics as the sample is flowing that can be time correlated with the characteristics of the samples 30 drawn by the system 10. The potentiometric module 12 can also be configured to gather and evaluate environmental metrics when the sample is flow is stopped. The potentiometric module 12 generally includes one or more ports 15 for attaching the IEEE compatible ion selective electrodes and sensors. Some of the electrodes can be adapted to measure characteristics of the sample drawn into our system. Other sensors can be connected with the system 10 through one of the ports 15 and then be remotely inserted to the water source 2. Examples of these sensors can include flow meters and temperature sensors. The information gathered from these electrodes/sensors can then be correlated, with data from the voltammetric measurements to give a full set of vital signs for that sample.

In one embodiment, the potentiometric module 12 can include up to five connections 15 for ion selective electrodes to measure specific characteristics in a holding cell or connection of other sensors. These sensors can include sensors such as for example a temperature probe or sensor 34. The sensor 34 can be connected via a suitable connection means 22 to the potentiometric module 12 and be adapted to be physically inserted into the sample or water source or elsewhere 2. For example, the sensor 34 could be inserted into a pipe stream of the water source 2 or hung off a buoy in the water source 2. The connection means 22 could include for example, a physical wire connector connection such as a cable, or a wireless optical or RF connection or coupling.

Figure 2:
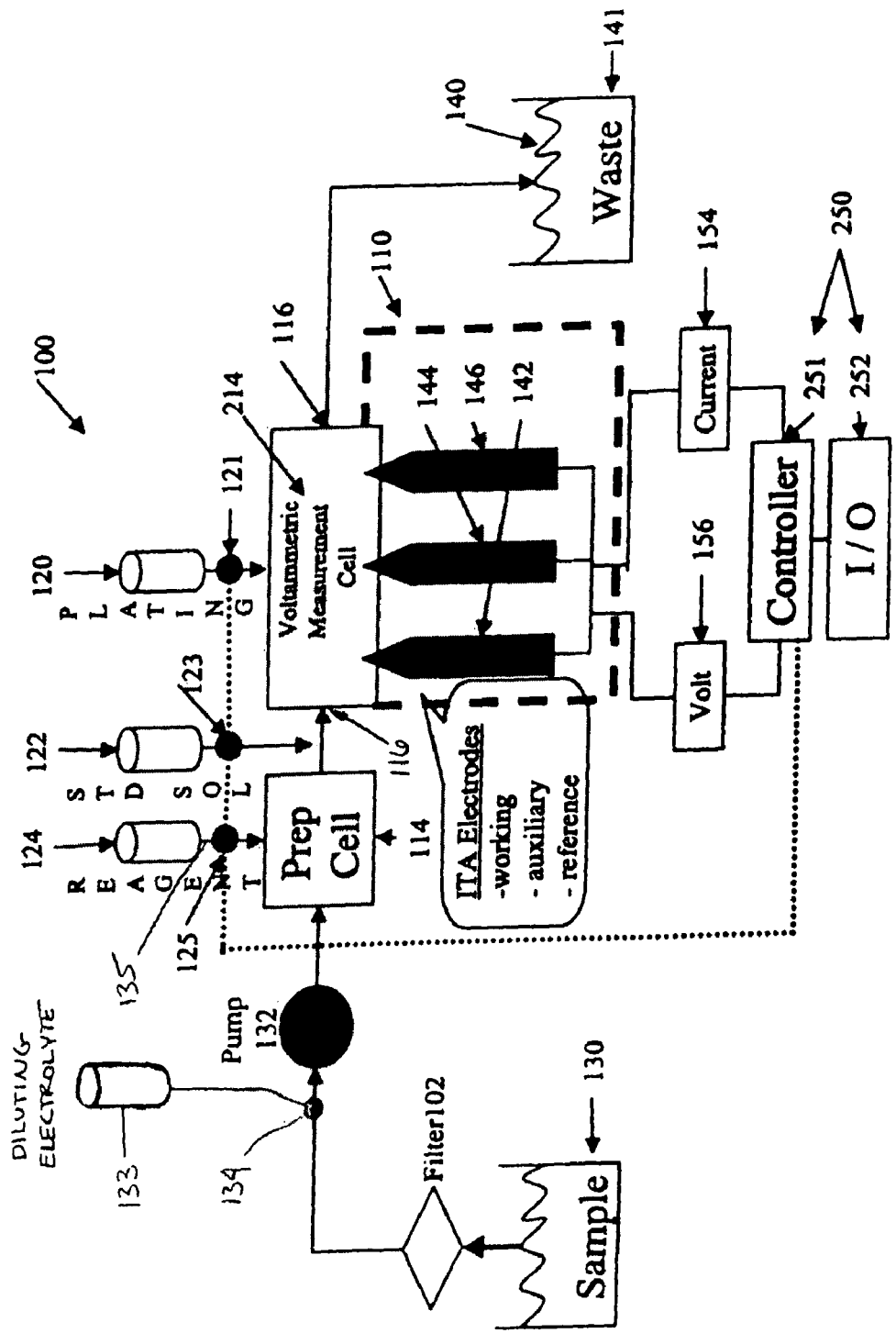
FIG. 2 is a schematic diagram of one embodiment of a system incorporating features of an embodiment.
Figure 10:
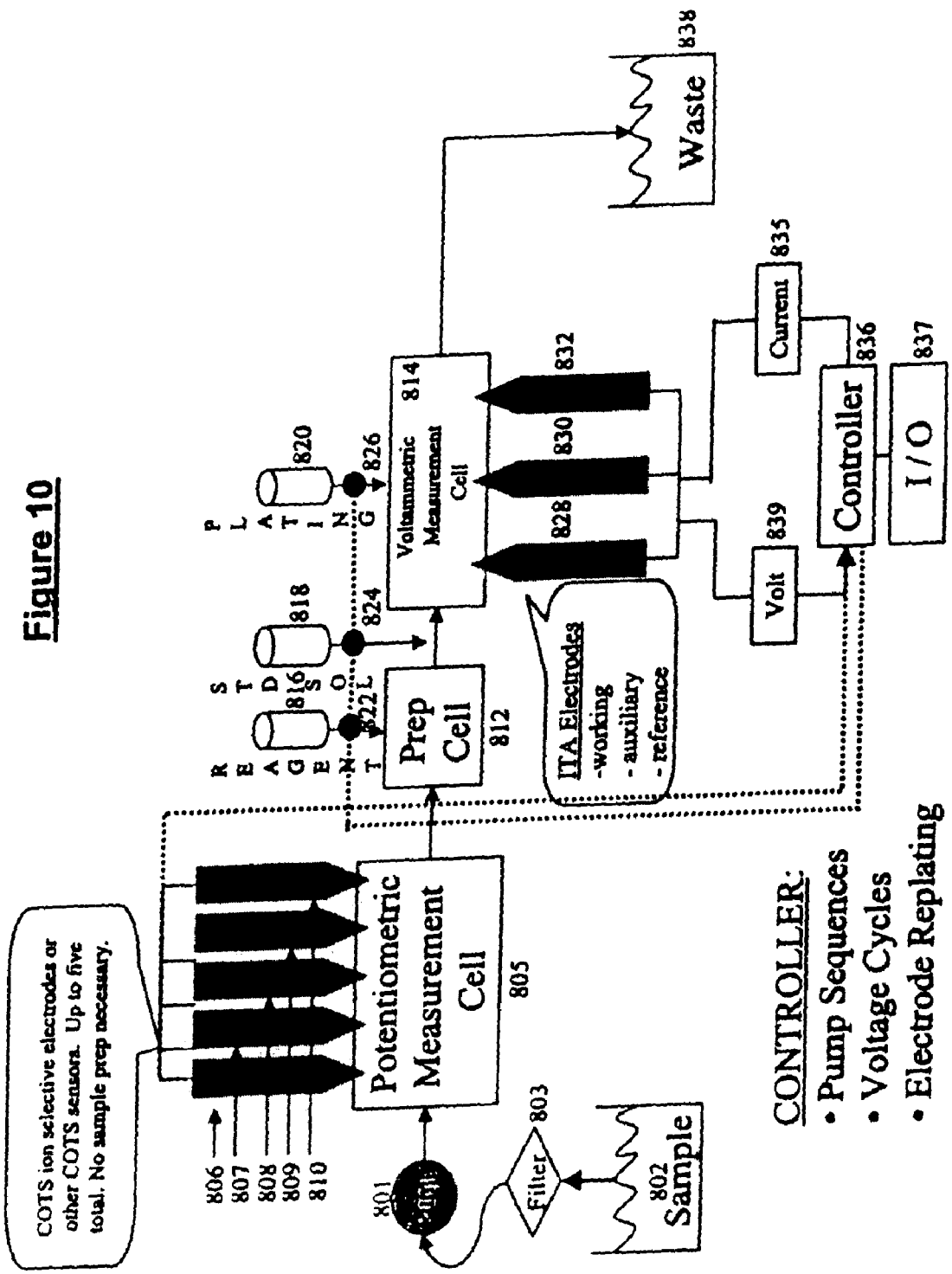
FIG. 10 is a block diagram of one embodiment of a system incorporating features of an embodiment.

The sample is then transferred to the sample preparation module or cell 14. Once the sample is in the preparation module 14, the sample is mixed with a preselected electrolyte solution. FIGS. 2 and 10 provide illustrations of how a reagent 124 and 816 can be introduced in the preparation cell 114/812. The sample preparation module 14 shown in FIG. 1 is generally adapted to process the species to be analyzed into an electroactive form and treats a sample 30 flowing into the module 14 with a reagent and then electrically stimulates the sample. The preparation of the sample is performed while the sample is flowing through the system. During the process of preparation, a number of things take place including stripping organics away, dissolving some possible particles of the contaminant of concern, any oxidizing and eliminating unwanted elements to minimize interference issue. The preparation module 14 receives the sample from the potentiometric module 12 via an inlet 19 controlled via pumps. The inlet 19 could include a controlled valve. In one embodiment, the system in FIG. 10 can include a system of pumps (822, 824, 826) and valves, such as for example, a hydraulic system.

In one embodiment, referring to FIG. 5, the preparation module 514 is a single chamber module that can be divided into two parts or sections 71, 72, with a semi-permeable membrane 80 separating the two sections 71, 72. In alternate embodiments the preparation module may have multiple chambers that can be subdivided by respective semi-permeable membranes. The semi-permeable membrane 80 is generally an ion exchange membrane adapted to facilitate the electrochemical oxidation of the sample. The membrane 80 (anion or cation exchange membrane) can be removed and inserted into the preparation module 514 and is selected for insertion into the preparation module 514 depending on the analysis to be performed so the solutions from both compartments of the module 514 will not mix with each other. For example, an anion exchange membrane may be used for metal ion analysis so that cations from the waste stream cannot move through the membrane to contaminate the sample. During the electrochemical oxidation of the sample current passes from a positively charged electrode in the sample flow through the membrane to a negatively charged electrode in the waste sample flow (on the other side of the membrane) because of the conductive fluid in the preparation module 514. The solvent also passes through the membrane 80 to the waste side of the preparation module 541 by osmosis to prevent contamination of the sample. As a result of the current flow and osmosis undesired metal, metalloid and nonmetal ionic species pass through the membrane 80 into the waste flow. As can be seen in FIG. 5, each portion 71, 72 of the module 70 can include an electrode, 77, 78 for preparing the sample 30 via a voltage that is applied across the electrodes. The electrodes 77, 78 can comprise carbon or graphite electrodes and are part of the sample preparation process. In the electrochemical preparation of the sample, the two graphite electrodes 77, 78 can be used in two chambers separated by the semi-permeable membrane. The voltage applied during the electrochemical preparation (e.g. oxidation or reduction of the sample) is automatically controlled by the system and is preprogrammed by the operator.

The sample flowing into the module 70 via inlet 73 is treated with a reagent and then electrochemically to convert the analyte to an electroactive form. The preparation will increase the conductivity of the solution, convert non electroactive species of the analyte to electroactive forms, and decrease interference from other elements in the sample 30. The electrolyte solution added to the sample, may consist of different reagents such as acid, base, salts, organic and inorganic chelating agents. The reagents are selected in accordance with characteristics of the sample. For example, the reagents include, but are not limited to, acids or non-acidic reagents such as sodium acetate, solochrome violet RS, and potassium nitrate. For example, disodium salt of L-tartaric acid and sodium hydroxide solution may be used in an Iron (III) analysis, sodium acetate solution and gallium (III)

atomic absorption grade solution may be used in a Zinc (II) analysis and hydrochloric acid may be used for a Selenium (IV) analysis and an Arsenic (III) (including Arsenic (V)) analysis. The flow rate of the reagents may be automatically or manually varied as they are added to the sample. If necessary, the second part of the additional sample preparation procedure may include an anodic or cathodic sample preparation procedure of analyte at specially regulated voltages. This step speeds up the processes of converting non electroactive species of the analyte to electroactive forms, and decreases interference, thus increasing the effectiveness of sample preparation and expanding the range of detection of the system to a parts per trillion level when the sample with the reagent is electrically stimulated as described above.

In one embodiment, referring to FIG. 5, the untreated sample flows in via tube 73 and the reagents are added to the inbound flowing compartment 71 of the preparation cell 70 via inlet tube 76. The sample with the reagent is electrically stimulated via the electrodes 77, 78. The treated sample then passes to the voltammetric cell 16 of FIG. 1, through outlet 74. The other side 72 of the cell 70 of FIG. 5, receives the waste from the voltammetric module 16 via inlet 79 and also draws waste material (e.g. undesired ionic species and stripped organics as described above) through the semi-permeable membrane 80 in the cell 70 via osmotic motion of the solvent. The outflow of the waste side 72 of the preparation cell 70 via outlet 75 is then sent to the waste container 40 of FIG. 1 and 420 of FIG. 4. In one embodiment, reagents can also be added after the sample preparation module 114, shown for example in FIG. 2, particularly when filters are part of the sample preparation module. Referring to FIG. 4, the inclusion of filters in the preparation module or cell 414 that might be otherwise found at the beginning of the sampling module of FIG. 1 allows the sequence of modules to be changed to suit specific user requirements.

The voltammetric module 16 of FIG. 1, and module 416 of FIG. 4 is generally adapted to identify and determine the concentration of the electro-active ions, to include inorganic and ion species in the sample using different modifications of the voltammetric method. The voltammetric modules 16, 214 (FIG. 2), and 416 (FIG. 4) can measure and analyze, for example, three different types of ions. In other embodiments any suitable number of different ions can be measured and analyzed. For example, the voltammetric module 16 and potentiommetric module 12 work independently to determine concentrations of the sample so that the report produced by the system includes the analyses by both modules 12, 16. The potentiometric system can include up to five ion-selective electrodes where each electrode determined its own ion. The ions can be metal, non-metal or metalloids for example. The combination of the potentiometric and voltammetric modules 12, 16 allows for the measurement and analysis of different types of ions at the same time.

When the ion concentration is determined in the voltammetric module 16, the sample flow is temporarily stopped to minimize the electrical noise of the measured signal. In this example, the sample flow is stopped for about 10 seconds for each measurement. In alternate embodiments, the sample flow may be stopped for any suitable length of time. For example, referring to FIG. 2, a voltammetric analysis, such as stripping analysis, is performed in a measurement cell 214 having three electrodes, namely, an auxiliary electrode 144, a reference electrode 146, and a working electrode 142. The three electrodes are placed in the measurement cell 214 in spaced-apart arrangement to minimize electrical noise and maximize a current measurement. In this example, the working electrode is as close as possible to the reference electrode. The working electrode is as far as possible from the auxiliary electrode. The distance between the working electrode and the auxiliary electrodes should be at least five times greater than the distance between the working electrode and the reference electrode. The working electrode is located between the auxiliary and reference electrode so that the current flow between the working and reference electrode does not interfere with the working electrode and auxiliary electrode circuit. The electrodes are configured so that the sample to be analyzed flows on the working electrode before the reference electrode. An electric potential or current is then applied across the auxiliary electrode 144 and the working electrode 146 to initiate reactions for measuring ion concentrations. The potential or current value is controlled versus the reference electrode (silver/silver chloride electrode).

The ions of the analyte to be analyzed or determined are electrochemical pre-concentrated on the working electrode surface during a given or predetermined time period. This is done by applying a sufficient negative or positive potential to the working electrode. The potential depends on the ion to be analyzed. The amount of the pre-concentrated analyte is proportional to the concentration of the analyzed ions in the sample. The time of pre-concentration may be any suitable time however, increasing the time of pre-concentration also increases the amount of analyte on the working electrode surface. The greater amount of analyte allows for a greater signal during stripping so that the detection limit of the analysis is expanded.

The following step is stripping off, oxidizing or reducing the pre-concentrated ions off of the working electrode by scanning the applied potential in the positive or negative direction. During the stripping, a current is produced. As the potential on the working electrode is varied over a specific range, and at a specified time duration, a varying current flows through the working electrode 142 surface as a result of oxidation/reduction reactions on it. The changes in current produced in the oxidation/reduction reactions is small, not sharp and difficult to read so the current is differentiated for easier analysis. The first derivative of current with respect to potential or the first derivative with respect to time can be calculated.

The resulting peak currents from the oxidation/reduction reactions are proportional to the concentration of each of the ions to be determined. The peak potential, which is specific to each of the ions, tells what ions are present in the solution. The peak current is used to calculate the derivative of the current over time. Because the current is proportional to potential in accordance with Ohm's Law, the current can be presented through potential (e.g. the potential is found using the current). As can be seen in FIG. 11, the potential can be used to calculate the derivative of the potential over time. Converting the current to potential amplifies the signal by reducing the noise on the voltammogram and making the peaks of the voltammogram sharper so that the detection limit is decreased to parts per trillion. Both derivatives, of current and potential over time, are proportional to the concentration. The position of the signals on voltammograms will be used for identification of the ions, and the magnitude of the signal will be used for determination of the concentration as can be seen in FIGS. 12 and 13. The different contaminates such as, for example, zinc, cadmium, lead and copper may appear on the voltammogram at different applied potentials as shown in FIG. 12. The magnitude of the signal S corresponds to the concentration of a respective contaminate. A voltage meter 156 and current meter 154 shown in FIG. 2 can be used to monitor the voltage/current change.

The voltammetric module 16 will determine a concentration of the species of interest. Actual contaminants such as arsenic and others can have multiple types of ions associated with it. These ions will have different characteristics. For example, arsenic typically has a variety of As+3 and As+5 ions dissolved in the sample. One is much more dangerous than the other, but there is tremendous value in knowing the presence and concentration of each type. Most systems can only tell you the presence of total arsenic, but very few can identify only As+3 and As+5 and/or the total of both As+3 and +5. In the arsenic problem this is significant because treatment requires that all arsenic be converted into As+5 before it can be removed. These different types of ions are generally called species, and the process that the system disclosed herein can perform is called speciation. It is a feature of the system to speciate electro-active ions.

Figure 3:
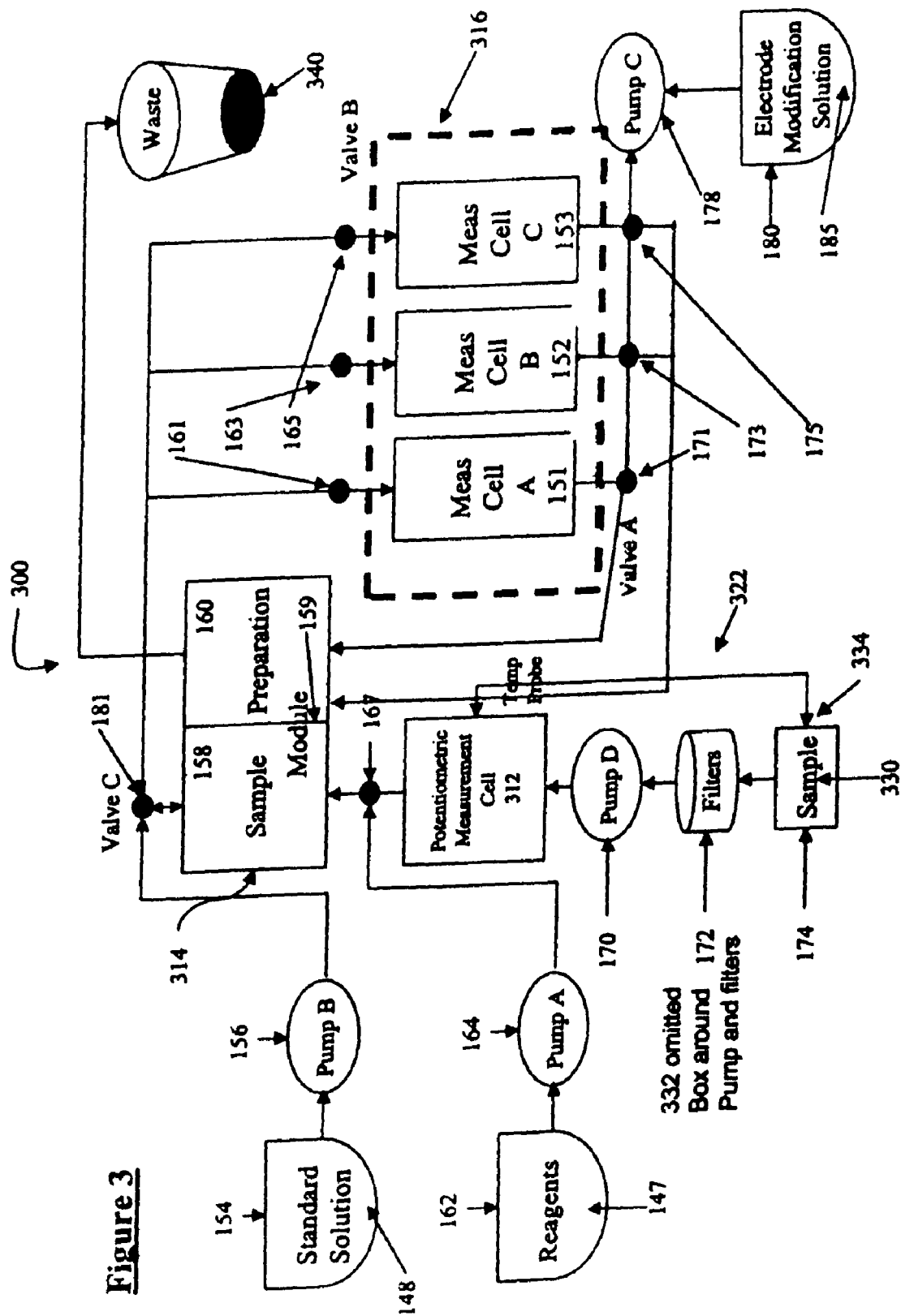
FIG. 3 is a schematic diagram of one embodiment of a system incorporating features of an embodiment.

The voltammetric module 16 of FIG. 2 is configured with at least one flow through cell meaning that the sample 30 can enter and exit the cell through separate inlets and outlets. In one embodiment it comprises a ceramic/teflon block with a channel that directs the sample through the block and over the exposed ends of each of the three electrodes (i.e. a working electrode, a reference electrode and an auxiliary electrode) that are configured in a unique relationship to minimize electrical noise and maximize the current measurement of the stripping process. The pumps control the rate of flow through the voltammetric cell, hence the volume, the system voltammetrically measures the concentration of the contaminant(s) of concern in "parts per billion" or more technically micrograms per liter. There are valves on either end of each flow through cell to stop the sample flow during measurement and the electrodes can be integrated into the cell. FIG. 3 depicts an embodiment of the system with up to three individual flow through cells 151-153 for the purpose of system redundancy and increased mean time between maintenance, while FIG. 2 depicts an embodiment of the system with more detail of one flow through cell 214 and the configuration with the integrated electrodes.

In one embodiment, referring to FIG. 2, a system 100 incorporating aspects of the exemplary embodiments can include a computerized device or system 250 for controlling the system 100. The system 250 can include a controller 251, such as for example a microcomputer or computer system adapted to manage and control sample 130 acquisition, sample preparation, sample flow, and sample presentation to the measurement cell 214, wave form generation, electrode plating, data acquisition, data processing, data evaluation, data visualization, data archiving, data reporting, process control, and alarm response. The control system 250 can be a microprocessor controlled system of sensors and control hardware and software adapted to monitor and manage contaminant flow through an aqueous treatment system.

The control system 250 is also adapted to control the sample, plating, reagent and standard solution pump work. Also, the control system 250 controls electrode modification operations, potentiometric measurements and potentials and times of electrode modification operation, sample preparation procedures, voltammetric measurements, sending the results to computer. The microprocessor receives the control parameters from the software program.

As shown in FIG. 2, in preparation for the stripping voltammetric analysis, the cell 214 should be properly prepared. The cell 214 can include a set 110 of three electrodes 142, 144 and 146. The electrodes 110 can include a working electrode 142, an auxiliary electrode 144 and a reference electrode 146. The choice of working electrode 142 depends on the type of analyte to be determined, and can be a specially modified graphite, gold, platinum, impregnated carbon, glassy carbon or iridium electrode. The auxiliary electrode 144 is a specially prepared graphite pressed into a polymer body, and the reference electrode 146 is a silver electrode pressed into a polymer body. In one embodiment, the electrodes can be composed of graphite, impregnated with organic and inorganic compounds, which are hermetically pressed into a polymer body and hermetically pressed into a respective cell. The stripping voltammetric or measurement cell 214 will work at this time on the preparation of the working electrode 142. For some of the elements, the plating preparation of the working electrode is not necessary. In one embodiment, if plating preparations are not necessary, a special radial button "NO" in the "plating" section in the "parameters window" of a control system input/output display 252 ("I/O") can be highlighted. If plating is necessary, the parameters of plating, such as potential and time of plating, should be shown on the "parameters window" of the I/O 252. During plating, a special solution from the plating solution chamber 120 will circulate through the stripping voltammetric cell 214. The plating solution composition varies from the type analyte that the system 100 is adapted to detect. Plating potential will be given to the working electrode 142 using a three electrode potentiostat scheme. Plating potential value and plating time may be varied by changing parameters of the "plating" section of the "Parameters" window in the computer 251. When the working electrode 142 is prepared, the plating solution will be pumped back to the plating chamber 120 and the prepared sample will go through the cell 214. The plating pump 121 will not work again, until new plating is required.

The system 100 starts a stripping voltammetric analysis, once it has taken a sample 130, filtered it 102, performed temperature and potentiometric measurements on the sample 130, initially prepared the electrodes 144-146, and filled the sample preparation chamber 114. The voltammetric measurements will be done using specially developed algorithms of stripping voltammetric analysis. At the beginning of each analysis the working electrode 142 will be cleaned by scanning linear potential from $E_{deposition}$ to $E_{final}$ multiple times. The potentials and number of scans may be varied through the "parameters" window of the software program. Next, the deposition step will be conducted. The deposition step may involve one or two different potentials given for certain amount of time. All potential values will be given versus the reference electrode. The deposition potential and time of the deposition may vary by using the "parameters" window of control system 250. Throughout the deposition step, the sample 130 will flow through the cell and directly past the working electrode 142. The next step, the measurement step, will require a complete halt of all sample flow. All system pumps 121, 123, 132 and 125 will be turned completely off and all valves (e.g. valves 116) near the stripping cell 214 will be closed, and the cell 214 should remain filled with solution. After a predetermined waiting period, for example ten seconds, the potential on the working electrode 142 will be linearly scanned from $E_{deposition}$ to $E_{initial}$ at a preselected rate. The system 100 is configured to analyze a derivative of current over time (dI/dT), a derivative of current over potential (dI/dV) and/or a derivative of potential over time (dV/dT). The derivative of current over potential is shown in FIG. 13 with respect to some exemplary contaminates. A mathematical analysis of the current derivative versus the potential derivative will be measured and compared and a voltammogram of the result will be stored in the memory of the device, and displayed on the operator screen, and/or transmitted to a central data archival system. In one embodiment, the voltammogram may be presented as a graph having dI/dV or dI/dT on the Y axis and potential (V) on the X axis (See FIG. 13). In another embodiment the first derivative of the calculated voltage (dV/dT) is presented on the Y axis while the applied potential (V) is presented on the X-axis. In other embodiments, the voltammogram can include any combination of the derivatives described above along any suitable axes.

In one embodiment referring to FIG. 2, the system 100 can include a container 122 with standard solution of analyte. After the previous step, a known amount of the standard solution will be added to the sample flow. The amount of standard solution added may be varied automatically through the "Parameters" window of the control device 250, or manually in the system. All measurements described above will then be repeated.

Figure 14:
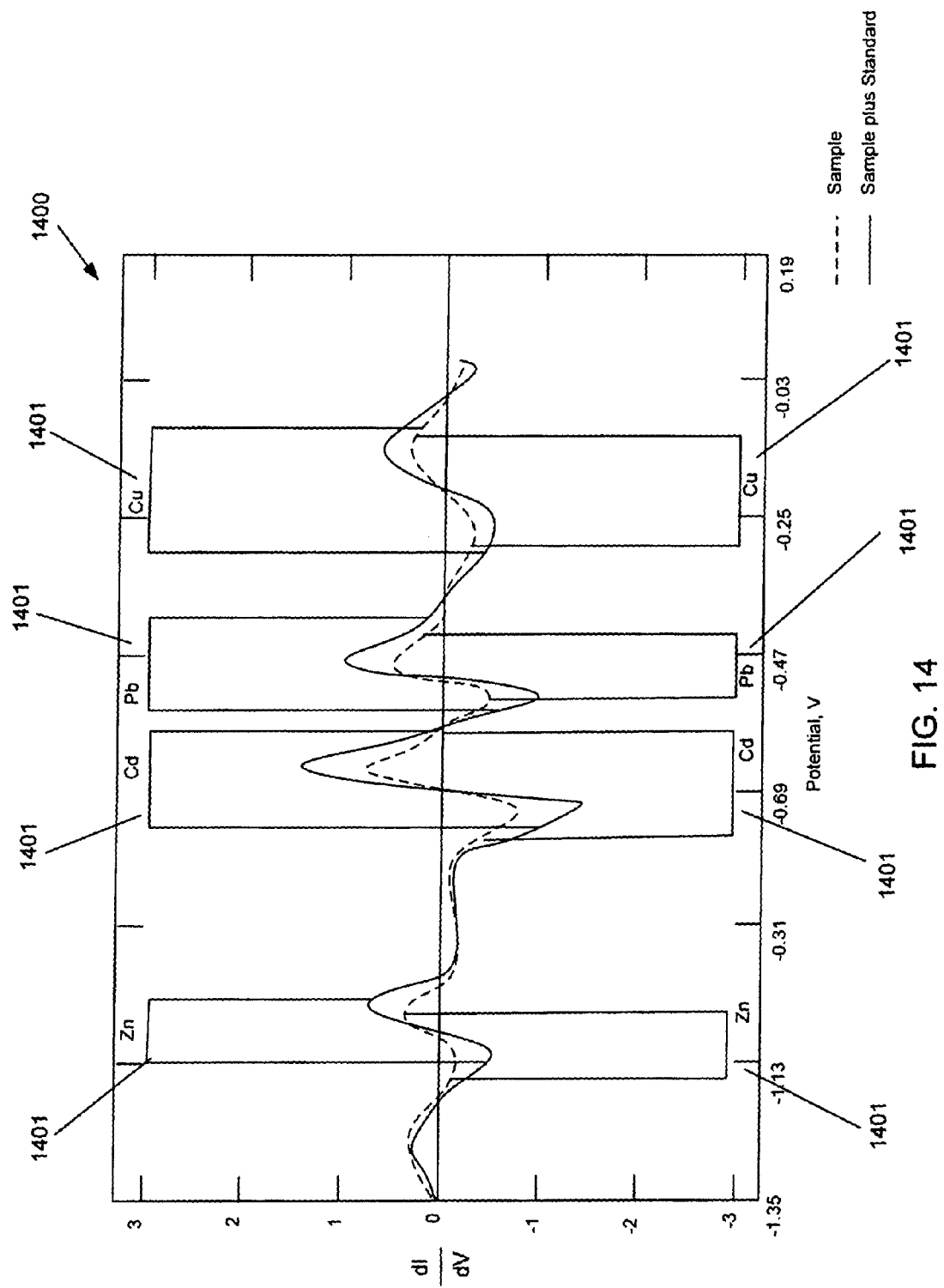

Two voltammograms of the sample, with and without standard additions, can then be recorded and displayed in, for example a voltammogram as can be seen in FIG. 14. In one embodiment, a window of the I/O 252 can have moveable boundaries 1401-1408, which can be used to select a signal to measure. The control device 250 will find the minimum and maximum amplitudes of each curve in the area of two boundaries and calculate the maximum amplitude of the desired signal in specific units. The high of the signal of sample and signal of the sample with standard addition will be used for calculation of ion concentration using a specially formulated mathematical formula.

The system 100 is adapted to continuously analyze solution. This means, when one cycle of potentiometric measurement is completed, the next stripping voltammetric steps will be repeated.

In one embodiment, the system 100 will automatically compare the value of the stripping signal of the sample with a predetermined value to determine if dilution is required. If the value is larger than a standard value, the system 100 can automatically use the dilution mode. In the dilution mode, the system 100 will automatically open or closed valves 134, 135 so that the sample pump 132 will be used for pumping the diluting electrolyte 133 and the reagent pump 125 will be substituted for and work as the sample pump. The valve 134 is shown in FIG. 2 as a two way valve but in other embodiments separates valves may be used for connecting pump 132 to the sample and diluting electrolyte 133. In other embodiments any suitable pumps may be reconfigured so that the diluting electrolyte 133 is added to the sample. The dilution ratio may be changed by changing the speed of the pump through a "Dilution parameters window" of the I/O 252 or manually. The voltammetric measurement procedures above will be the same. In the calculations of the concentrations, a special dilution mode formula will be used.

After the sample is analyzed in the measuring cell 214, the solutions will be guided to the waste water section 141. In the waste water section 141, the water 140 may be collected in the container or bottle 141 or cleaned using special columns with adsorbents or ion-exchange resins.

The computer or control system 250 attached to the system will have a program for preparation of the reports. Data will be shown corresponding to the time of the analysis, and may be archived for further analysis.

The system 100 can also include alarms or warnings. If the contaminant concentration being monitored is greater or less than a predetermined value, the system 100 communicates to a controller to initiate alarms, redirects water flow into a holding tank, notifies key personnel, and provides signal inputs to system control software to affect contaminant removal processes.

The system 100 can also include a self test mode to be able to test key parameters to determine operational status.

Referring to FIG. 3, the voltammetric analysis module 316 can include up to three flow-through cells 151, 152 and 153 for voltammetric measurements. Each of these cells has a working electrode, a reference electrode and an auxiliary electrode as will be described below with respect to FIG. 2. There are valves on either end of each cell 151-153 for stopping the flow of the sample during the voltammetric measurements, and the electrodes are integrated directly into the cell itself. The addition of the standard solution 148 and plating solution 185 (i.e. modification solution) are injected through the valves 161, 163 and 165 directly up stream from the flow through cells 151-153. Having more than one cell 151-153 allows for greater flexibility and time between servicing. In order to extend the time between system services, the system can be automatically selected to switch from one cell to another when the efficiency of one cell reaches a predetermined limit. The cells 151-153 can also be changed manually by the operator, if necessary using the "start new cell" option in the "parameters" window of the users software.

The sample pump 170 shown in FIG. 3 will contain a pump connected to a specially designed electronics circuit. The speed of the pump 170 may be varied manually and automatically. The filtration of the sample 330 occurs through specially constructed filter unit 172. The combination of filters may be changed in accordance with tasks of the analysis. The potentiometric and temperature measuring unit 312 is adapted to conduct a potentiometric analysis of the sample 330 drawn using ion-selective electrodes. The potentiometric cell 312 contains a special chamber with ion-selective electrodes such as those shown in FIG. 5. The electrodes may be changed in accordance with tasks of the analysis. The electrodes are connected to a specially designed electronic circuit, which is managed by a microprocessor based controller. The potentiometric chamber 312 can also have a level sensor, which is connected to a controller and will give signal based on sample presence. The temperature sensor 334 determines the temperature of the sample 330 and as can be seen in FIG. 3, is remotely located from the potentiometric unit 312 and may be connected through an isolated electrical cord 322.

After potentiometric measurements in unit 312, the sample will go to the preparation module 314. The preparation module 314 is a single chamber module that can divided into two parts or compartments 158, 160 separated by a semi permeable membrane 159 similar to the exemplary preparation module shown in FIG. 5. Referring to FIG. 3, the sample and necessary reagents will flow into the chamber 158, where the mixing occurs. The speed of pump 156 may be varied automatically and manually. Special design of the electrodes 77, 78 shown in FIG. 5 and connections will prevent contamination of the sample from connectors and provide hermetic isolation of the cell. In this example, the electrodes 77, 78 are graphite electrodes, where one electrode is located in each of the parts 158, 160 and are connected to an electronics circuit, which will give potential from −10V up to 10V. The sample will be treated anodically or cathodically in accordance with a special algorithm. The algorithm or anodic/cathodic treatment of the sample can be controlled by the microcontroller and may be varied through the "sample preparation voltage" in the "parameters" window of the software program. The reagent pump 164 additionally will be monitored by the controller. The speed of the pump 164 can be changed manually and automatically by changing "pump parameters" in the software window. The second part 160 of the preparation cell 314 will be filled by sample flowing back from the voltammetric cell 316.

As shown in FIG. 2, the voltammetric flow through cell 214 can contain three electrodes (i.e. working electrode, reference electrode and auxiliary electrode). The working electrode 142 can be a specially designed graphite electrode in a polymer body. The auxiliary electrode 144 can be a specially designed graphite electrode. The reference electrode 146 can be a silver wire in a polymer body. The cell 214 has a geometric groove through it and is configured so that a portion of the electrodes 142-146 extends into the groove. The solution flows through the groove and comes into contact with the portions of the electrodes 142-146 that extend into the groove. The groove can be any suitable dimension. In the preferred embodiment the groove can be approximately ½ millimeter (0.5 mm) in cross-width and ½ millimeter (0.5 mm) in depth, running down the middle of the flow through cell.

Referring to FIGS. 2 and 4, in order to prepare the working electrode 142 in the voltammetric analysis cell 214 for analysis, plating solution 120 is pumped in by means of the pump 121. The pump is monitored through the electronic circuit and the speed of the pump 121 can be changed manually or automatically. This can include changing pump parameters in the software program of control device 250. The speed of the pump 121 will be monitored by the system controller. The electrode surface is modified in accordance with a special algorithm and potentials/currents applied to the working, auxiliary, and reference electrodes 142-146 in the measuring cell 214 using a three electrodes electronics scheme. The algorithms of the applied potential/current are controlled by the controller. The algorithm of the electrode modification can be ordered through "plating parameters" of the "parameters" window.

The voltammetric measurement of the sample flowing through the cell 214 of FIG. 2 will be done in accordance with an algorithm which will be monitored by a micro controller and can be changed through a software window. The parameters of voltammetric measurements include changing the deposition potential from about −2.5V to about +2V, initial potential from about −2.5V to about +2V, final potential from about −2.5V to about +2.0V, time of deposition, linear scan rate can vary from about 0.05V/sec to about 1V per second, a quiet time of about 10 sec, type of linear-scan, number of cleaning scans from about 1 to about 50. Anodic and/or cathodic stripping voltammetric measurements will be available.

Figure 6A:
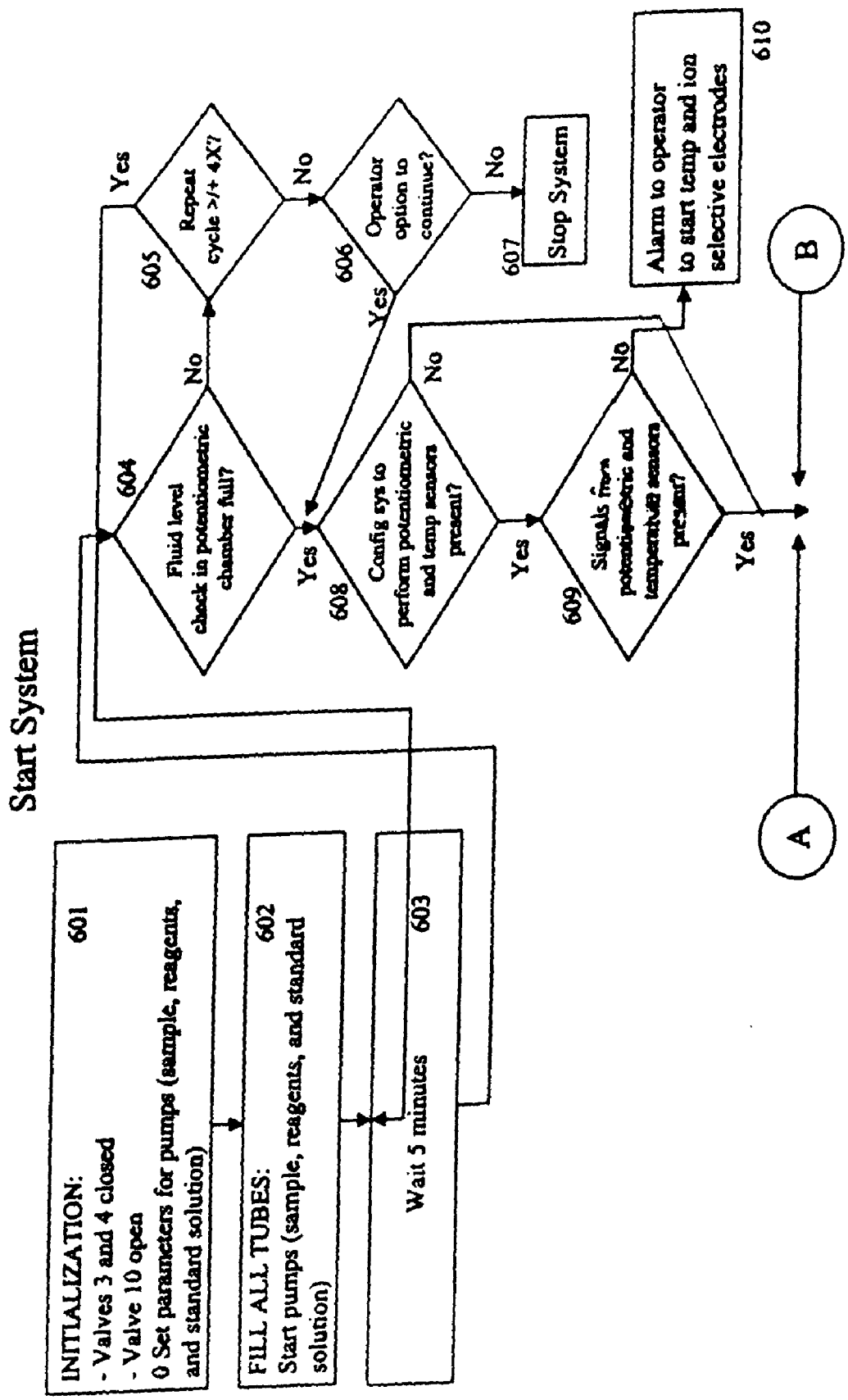
FIGS. 6A, 6B and 6C are a flow chart illustrating one embodiment of a method incorporating features of an embodiment.
Figure 6B:
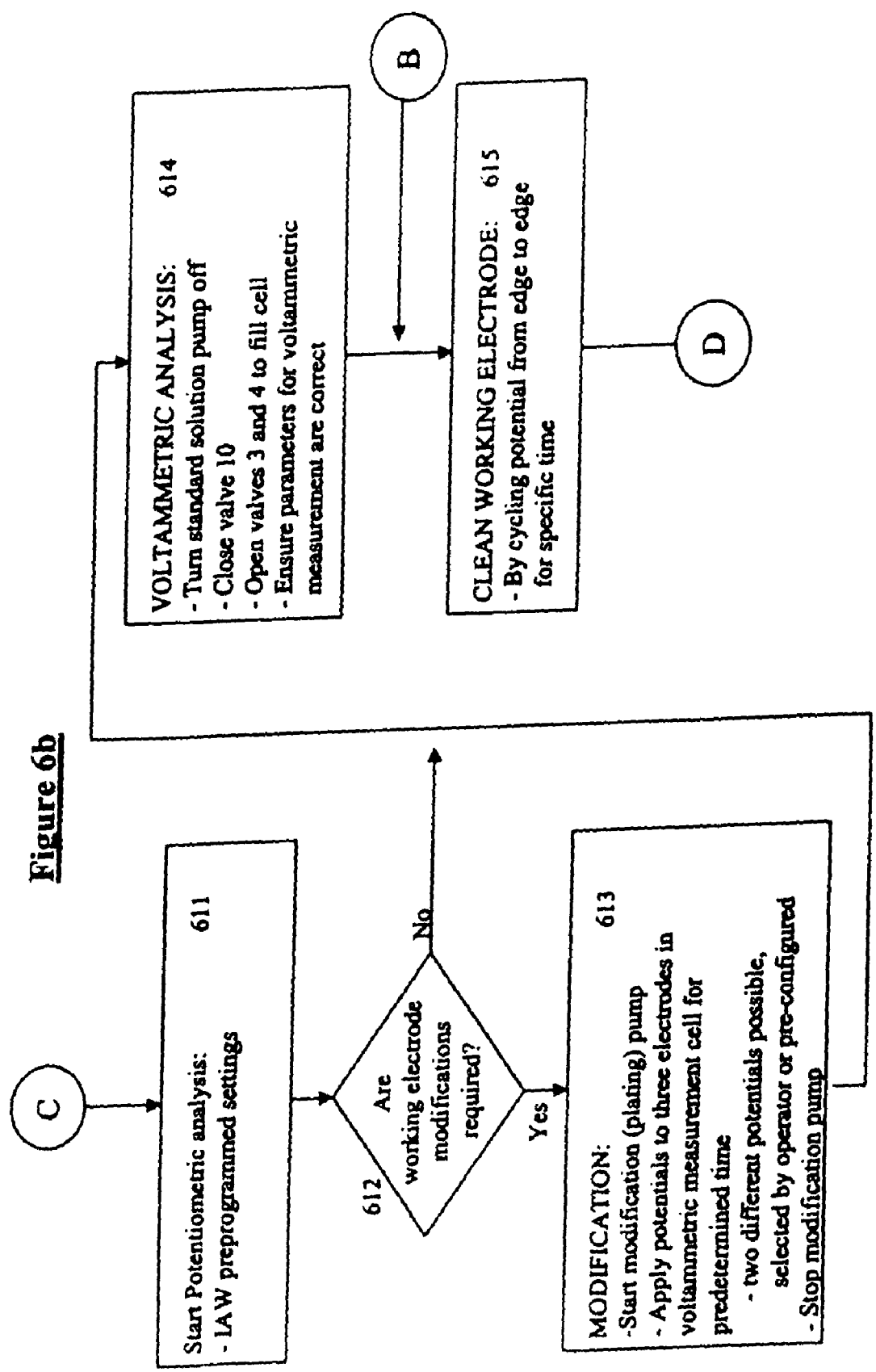
Figure 6C:
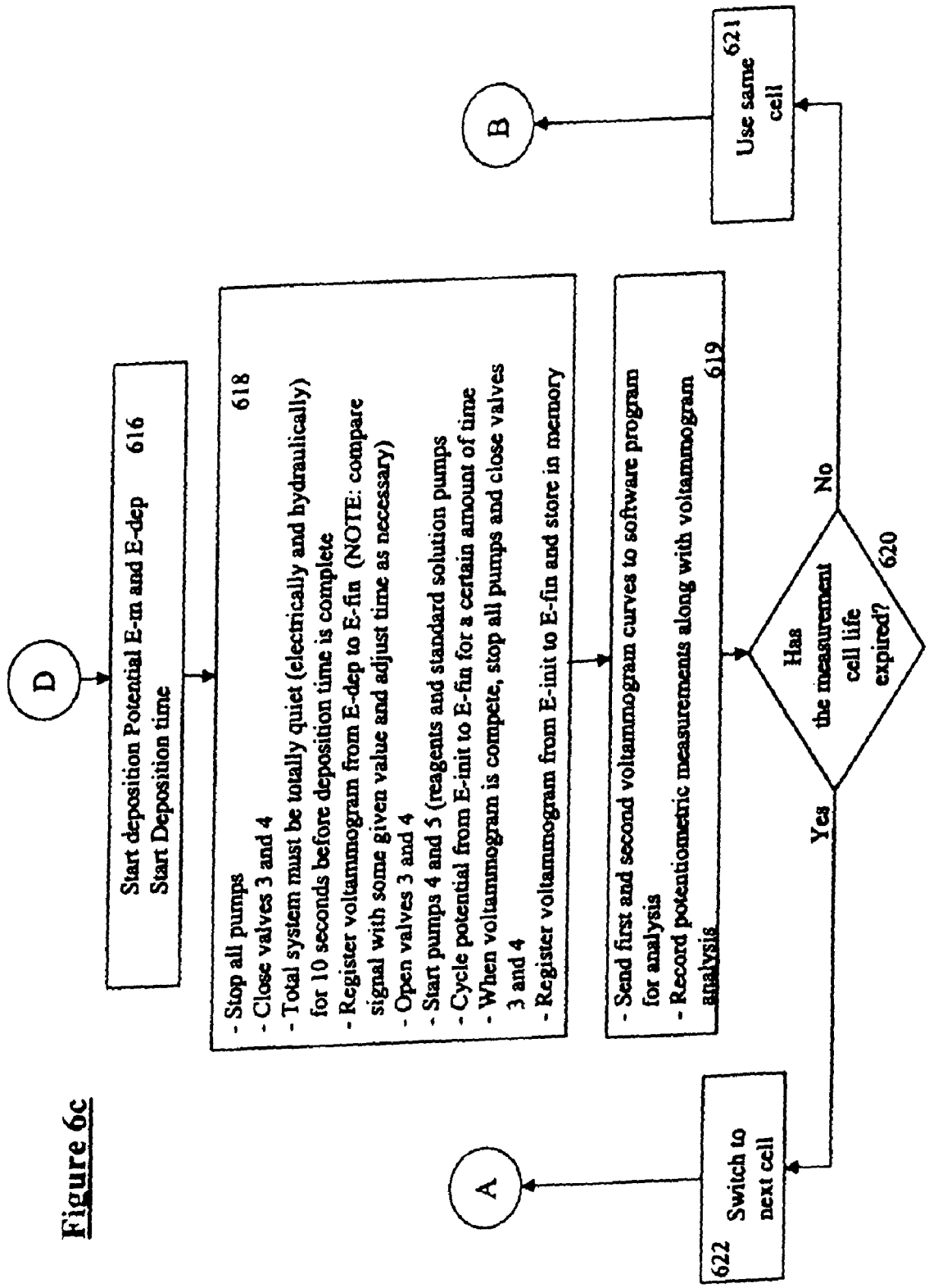

Referring to FIGS. 6A-6C, one embodiment of a method of stripping voltammetric measurements is shown. The initialization step (601) includes pre-concentration of the analyte on the surface of the electrode as given in the system parameters (deposition potential, time of deposition). The sample, which is prepared for analysis, will flow through the preparation cell 114 in this step. All pumps (164, 156 and 178 of FIG. 3) can be stopped and the valves 116 of the measuring cell 214 will be closed. The sample will not flow through the cell 214, but the cell 214 will be filled with the sample. A linear change of the potential from an initial potential to a final potential is applied. At this step the current versus voltage curve, with respect to a time period over which the measurement was taken, will be registered. The electrode is electrochemically cleaned. Voltammetric measurements of sample with standard addition will occur. The standard solution pump 123 will be automatically turned on and voltammetric measurements described in previous part will be repeated.

In one embodiment, the microprocessor will send the results of the measurements to the memory of the computer 151. After this the new cycles of measurements will be done. The software program has special boundaries (See FIG. 14), which will be moved by the operator to identify the peaks to be measured. The peaks should be identified only one time, since the position of the peaks are the same, the program will use it for the following calculations. If necessary, the boundaries may be moved. The program will find signal values (value between max and min current inside of the boundaries) and calculate the results using special formulas for standard addition method. The program will prepare reports and send it to memory.

In one embodiment, the central controller 251 is a microprocessor device that is adapted to archive all system measurement data, analyze all data according to predetermined criteria, and then affect water management control measures accordingly. The central controller station 251 and I/O unit 252 (see FIG. 10—controller 836, I/O 837) and allows an operator to review data from all measurement stations, as well as visualize, on a conceptual map, all systems under control. The central control 251 can include software that allows for storing, analyzing, and displaying all data collected throughout the system. It allows the import of data from other sources and the correlation of all data on printed reports and database files. The software can also incorporate a full featured statistics, spreadsheet, and graphics program for analysis and reporting purposes. The system controller 251 can direct the emergency response in the case of the systems detecting unacceptable levels of contaminants in the discharge through such actions as automatically notifying personnel, activating alarms, and redirecting water by switching valves. In one embodiment, the central control 251 is a WINDOWS™ based system. The system 250 can display certain "windows" to the user depending on the state of the system 100 and the particular application or measurement state.

Figure 9:
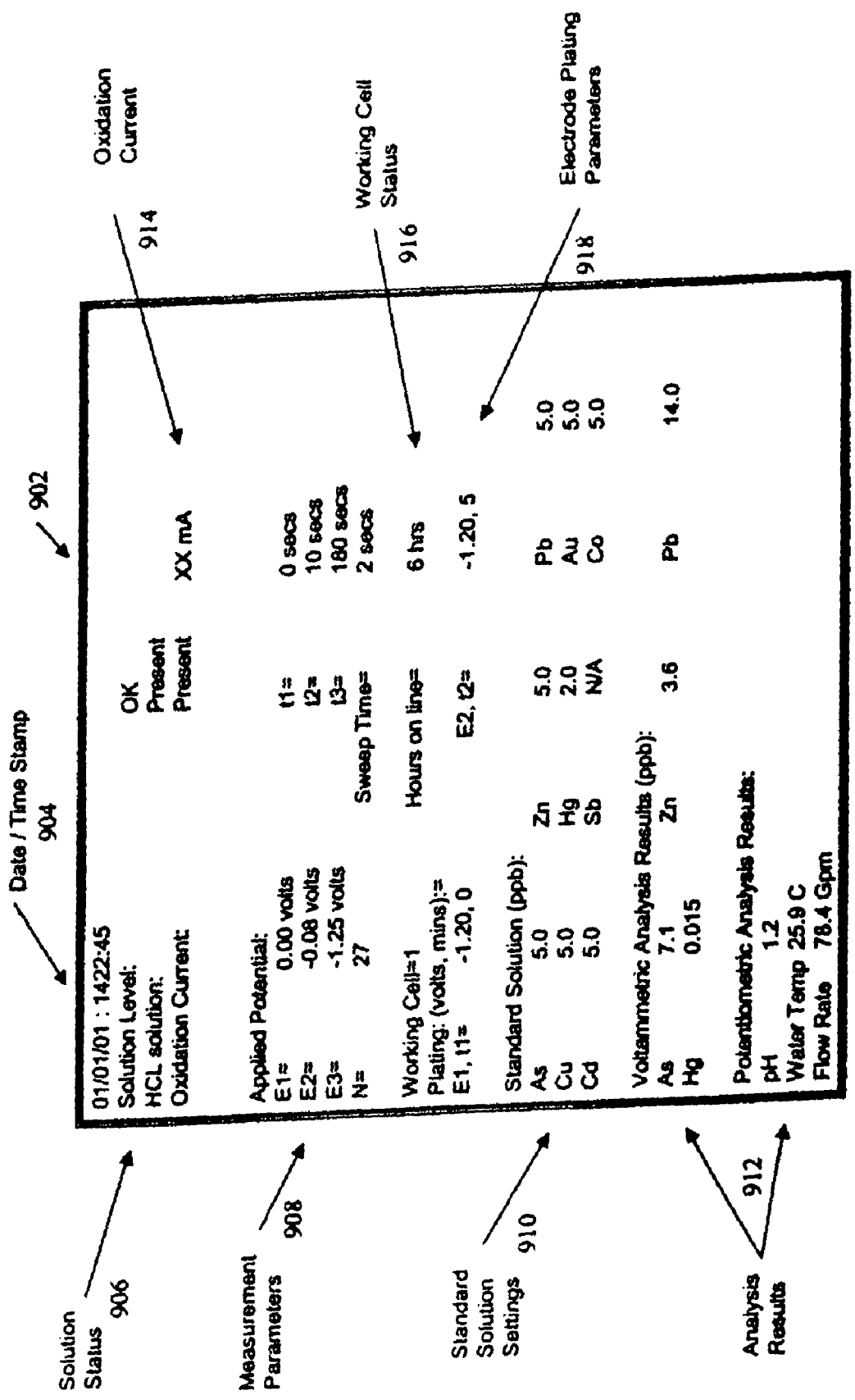
FIG. 9 is an illustration of an exemplary system data display window for a system incorporating features of an embodiment.

The software program can have one or more windows. One of them can be a "System Data Display" window such as that illustrated in FIG. 9. The window 902 can include blocks for pump parameters, potentiometric measurements parameters 914, working cell status 916, sample preparation parameters 906, stripping voltammetric measurements parameters 908, date/time stamp information 904, standard solution 910 and plating parameters 918. Each block will show possible values of the parameters and allow the operator can select the values. If some values are not selected when the system is initiated, the program will prompt the operator to add any necessary parameters. The program can also have an "analysis results" window or block 912. In this window the voltammogram of sample and sample with standard addition will be shown, also the results of potentiometric and temperature measurement will be displayed. This window will have at least three sets of boundaries. The user will be able to move the boundaries to isolate the peaks which will be used to calculate concentrations levels. The software will have a special program for calculation of signal value, which is a value between max and min of the signal, and also the program for calculation of concentration using special formula for calculation based on standard addition value.

Referring to FIGS. 3 and 6, one method of operating a system 300 incorporating aspects of the exemplary embodiments is illustrated. As shown in FIG. 3, the system 300 generally comprises a single chamber sample preparation module 314 that is divided into two compartments 158 and 160 via a semipermeable membrane 159. The potentiometric measurement cell 312 receives the liquid sample 174 that has passed through the pump 170 and filters 172. One or more temperature probes 334 monitors the temperature of the sample 330 in the sample container 174 and in the potentiometric measurement cell 312. As shown in FIG. 3, the voltammetric module 316 can comprise up to three flow through measurement cells illustrated as 151, 152 and 153. A liquid waste module or container 340 is adapted to receive the sample after it has been processed and analyzed.

The system 300 shown in FIG. 3, includes a reagents module or container 162, a standard solution module or container 154 and an electrode modification solution module or container 180. The reagent 147 is pumped from the reagents module 162 via pump 164 to a valve 167 to be combined with the sample as it passes from the potentiometric measurement cell 312 to the first cell 158 of the sample preparation module 314. A standard solution 148 can be pumped from the standard solution module 154 via pump 156 to the first part 158 of the sample preparation module 314 via a valve 181. The electrode modification solution 185 can be added to any one of the flow through voltammetric measurement cells 151, 152 or 153, via valves 161, 163, 165, respectively. Valves 171, 173 and 175 can also control the flow of the electrode modification solution 185 back to the container 180 or to the second part 160 of the preparation module 314. A pump 178 is shown to pump the electrode modification solution 185 to and from the measurement cells 151, 152 and 153.

In one embodiment, referring to FIGS. 3 and 6, the system is initialized 601 and valves 161, 163, 165 and 171, 173 and 175 are closed. Valve 181 is opened to direct the flow of standard solution into section 158 of the sample preparation module 314. In an embodiment of a system 100 controlled by a control system 250 shown in FIG. 2, the program is started and all parameters of the analysis should be adjusted in the program and after that the program will await a signal from the microcontroller. The service person can go to the system and start the system by pushing a "start" button. For example, the microprocessor will close valves 161-165, and valves 171-175. The microprocessor will send a signal to the software that the system has started and check the parameters of the pumps. The sample pump 170, standard solution pump 156 and reagent pump 164 will be started. The system will then pause (block 603) for approximately 5 minutes to allow sufficient time to fill all tubes (block 602) with solutions and to fill the chambers of the measurement cells 316 with sample or solution that is to be added to the sample (block 604). In five minutes, the status of the level sensor in the potentiometric chamber 312 can be checked. If the level sensor shows that the chamber 312 was not filled, the system will wait again 5 minutes and after that will check the status of the level sensor again. In case of a failed signal, this cycle can be repeated for example 4 times (block 605), after this a warning sound signal and sign to check the sample pump and level sensor on potentiometric chamber can be sent. Also, a warning signal is sent to the panel of the device 250 to flash a lamp. If the system is not stopped at this moment (blocks 606 and 607), manually or through the computer, the system will proceed to the next block 608. The system will also proceed to block 608 if system has a positive signal (the potentiometric chamber is filled). In block 608, the system will identify if the potentiometric or temperature sensors are necessary. If yes, the system will take first measurements, to be sure that signals from the sensors exist (block 609). If signals do not exist, or are out of range the lamp on the device panel will flash and a warning sign "check potentiometric sensors and/or temperature sensors" will appear (block 610). If signals are acceptable, the system will proceed to the same block 611 and start the potentiometric analysis. The microcontroller will check if modification of the working electrode in the voltammetric flow through cell is necessary (block 612). If it is necessary, the microcontroller will start the pump 178 to transfer the modification solution 185, also referred to as the plating solution into one or more of the measurement cells 151-153 for plating the electrodes via valves 171, 173, 175, which are temporarily opened (block 613). In other embodiments, the electrode modification solution 185 can be transferred into the measurement cells 151-153 in any suitable manner. At the same time the voltage parameters of the modification and time duration of every voltage will be checked by the microcontroller. The microcontroller will remember both times and voltages. When the first time is over, it will go immediately to the second time. When the timer shows that the second time is over, the microcontroller will stop pump 178, stop pump 156, open valves 161-165 and 171-175 and start voltammetric measurements (block 614). The cycle of voltammetric measurements include starting the cleaning of the electrode (block 615) from $E_{initial}$ to $E_{Final}$, then a preconcentration step (block 616). The preconcentration step will have two potentials available $E_{Deposition}$ and $E_{initial}$. After preconcentration is finished the microcontroller will proceed to the next block 618, referred to as "quiet" step. At block 618, the potential E initial will be kept on the working electrode, but all pumps (170 and 164 should be "off", and pump 156 is "off" already from the previous step), the valves 161-165 and 171-175 are also off or closed. After 10 seconds of quiet time, the linear scan of the voltage from $E_{Initial}$ to $E_{Final}$ will be done. The current versus voltage with respect to the scanning time will be recorded and stored in the memory of the microcontroller (block 619). The current versus voltage may be in the form of a first voltammogram, which corresponds to the sample. Then the valves 161-165 and 171-175 will be opened and pumps 170, 164 and 156 will be "on" with the speed of each shown on the I/O 252. The cleaning of the working electrode from $E_{Initial}$ to $E_{Final}$ will be done and the whole measuring process will be repeated. The second voltammogram, which corresponds to the sample with standard addition will be sent to the computer. At the same time the potentiometric measurements will be done and sent with the second voltammogram or with two voltammograms. So, with this algorithm the potentiometric measurements will be done with the same frequency as voltammetric measurements. When all information is sent to the computer the microcontroller will stop pump 156 and the process of stripping voltammetric measurements will start again (block 621). At the same time the microcontroller will monitor the efficient life for each of the flow through voltammetric measurement cells (block 620). When the efficiency of each voltammetric flow through cell reaches a predetermined level the microprocessor will switch to the second cell 152 (block 622). The cells 151-153 also may be switched manually through the software. If the operator clicks on the button "switch the cell", the program automatically will go to the next cell, and the process starts. For the second cell 152 everything is the same, except, that instead of valve 151 and 171, it will be 152 and 173, and for cell three it will be 153 and 175.

In one embodiment, referring to FIG. 7, one embodiment of a system 700 incorporating aspects of the exemplary embodiments could include two systems 710, 720, similar to the system 10 shown in FIG. 1. A water treatment system 730 is located between the two systems 710, 720. Referring to FIG. 7, each system 710, 720, generally includes a potentiometric module 12, a sample preparation module 14 and a voltammetric analysis cell 16 as shown and described with reference to FIGS. 1-3. Each system 710, 720 can be adapted or "programmed" to forward certain information or measurements to an external controller or system that is controlling the treatment process. For example, in a large water treatment plant there is typically one main controller that monitors and controls the whole plant. A series of small controllers could be in charge of certain subprocesses. In a large treatment plant with multiple waste streams, and treatment processes, the disclosed embodiments could be expanded to provide a network of individual sensors (complete systems). Each "individual" system can be adapted to "talk" or communicate with a controller in the network identified as the master controller. The master controller can communicate with the plant process control system that will then manipulate the treatment process based on inputs from the system of sensors integrated throughout the treatment process.

These two systems 710, 720, one upstream from the treatment process center 730 and the other downstream of the treatment process, communicate with the treatment process controller to effect the efficiency of the treatment process and to ensure that overall discharge limits are not exceeded. This system will usually be interconnected with multiple other systems in a treatment plant. This system of systems then will contribute to the overall control of the treatment processes throughout the plant. The system 700 is generally adapted to detect contaminants and water characteristics in a water treatment process stream, both before 740 and after 750 the treatment procedure, and the correlation of these water characteristics measurements with a set of predetermined response tables that will affect the electrical and mechanical manipulation of treatment functions in the plant 730. Possible responses to data correlation could include valves to redirect water that is over discharge limits for specific contaminants, activation of alarms, direct input to treatment control process for removal of contaminants, automatic logging of all data collected, etc. The disclosed embodiments provide a fully capable system to monitor and manage the water treatment process variables and to be able to respond automatically with predetermined actions to control the functions within the process. Additionally, the disclosed embodiments shall allow an operator to monitor the operation of a multi sensor system and dynamically reconfigure response levels and actions for each sensor and data output recipient module.

The disclosed embodiments are viable in either a standalone configuration or integrated into a system of systems. In this integrated mode as shown in FIG. 7, the disclosed embodiments can comprise of a system 700 of at least two Stripping Voltammetric measurement devices for the detection of trace contaminants, with up to five potentiometric ion selective electrodes associated with each device to measure other sample characteristics. Each device shall consist of a structure for acquiring the sample for analysis of trace contaminants, a structure for real time measurement up to five other water characteristics in the sample, a structure for rapidly measuring contaminants in the sample, a structure for archiving data from the measurements, and a method for transmitting the data to a central control station. Each device shall be able to detect multiple elements and species down to at least 5 parts per trillion.

Each pair of devices working in conjunction upstream (740) and downstream (750) of a treatment process will communicate with the treatment process controls to affect the treatment additives and to optimize their efficiency. In addition to working with the treatment process controls, each device shall communicate with the central controller to archive measurement data.

The disclosed embodiments, in an integrated mode shown in FIG. 7, provides near real time water management system, measuring water quality parameters to include but not limited to pH, temperature, oxidation and/or reduction potential, alkalinity, and contaminant of concern concentration. Primary advantages of the disclosed embodiments are those of reduced analysis time, reduced costs, lower detection limits, higher selectivity, increased sensitivity, minimal sample preparation, inclusive data management, flexible process control, and on-line measurement capabilities over current methods.

In one embodiment, referring to FIGS. 2 and 10, the cell 214 and 814 is adapted to direct a supporting electrolyte flow through the cell while immersing the electrode system 110 (FIG. 10 electrodes 828, 830, 832), in the supporting electrolyte. As shown in FIG. 2, the cell 214 can include flow injector means from the hydraulics directing electrolyte from the sample preparation cell for injecting a flow of sample electrolyte through the cell 214 and onto the working electrode 142 when supported in the voltammetric measurement flow through cell 214.

The flow of electrolytes through the cell 214 is adapted to maximize the exposure of electrolyte to the electrodes while minimizing flow turbulence.

In one embodiment, referring to FIG. 10, the sample fluid 802 is filtered through filter 803 and pumped via pump 801 into a potentiometric measurement cell 805. The potentiometric measurement cell 805 includes up to five Commercial Off The Shelf (COTS) IEEE compatible ion selective electrodes 806-810, or other COTS sensors. In this embodiment, sample preparation is not necessary. The sample going into the cell will have standard solution 818 injected into the flow, and the plating solution 820 will be applied directly to the voltammetric cell. The controller 836 controls the COTS sensors 806-810, the voltage and current signals 835, 839 to the electrodes 828, 830, 832 in the cell 814, as well as the addition of the standard and plating solutions 818 and 820. Once the cell 814 has completed the voltammetric measurements, the sample will proceed to the waste container 838.

Figure 8:
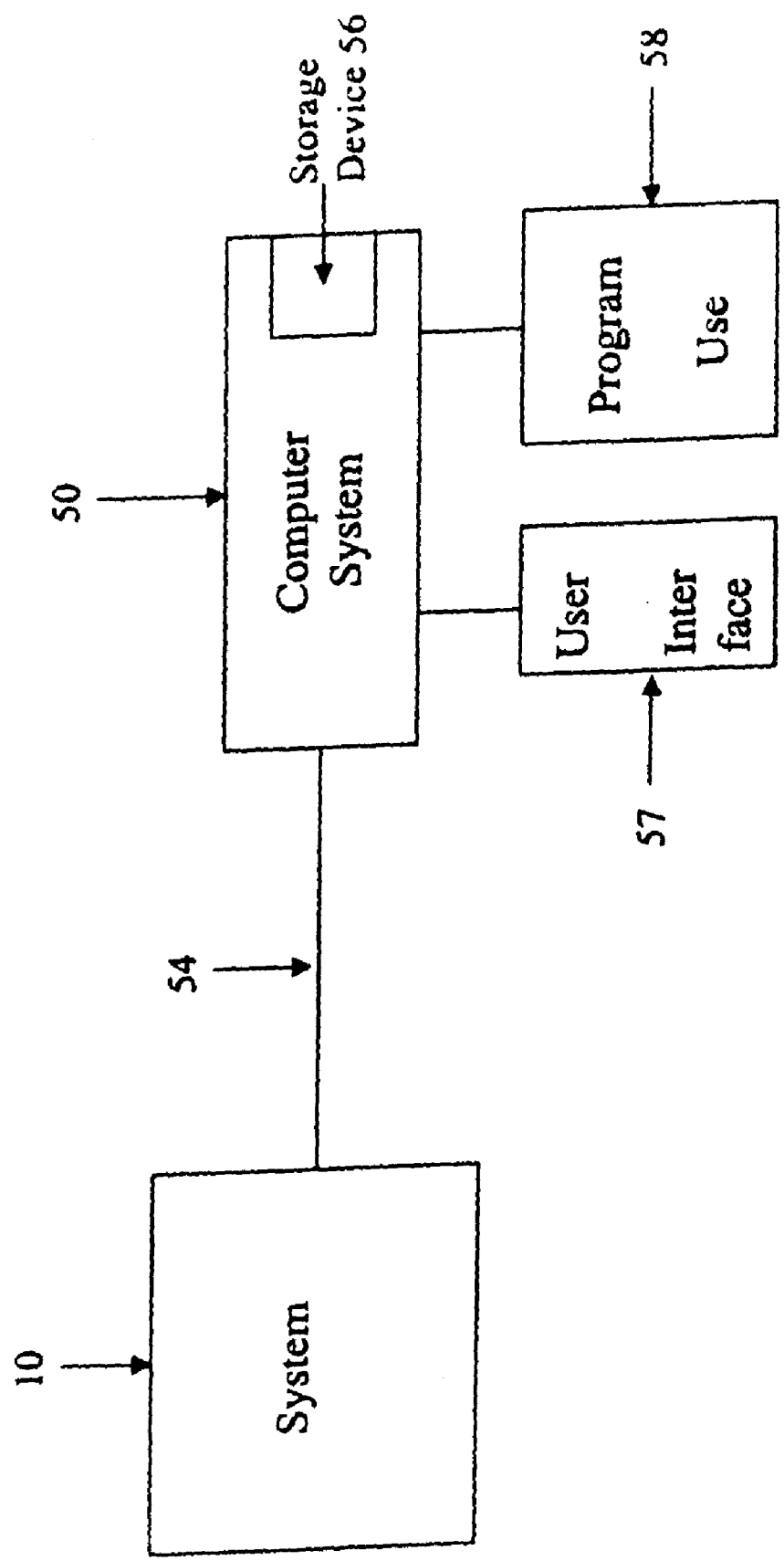
FIG. 8 is a block diagram of one embodiment of an architecture that can be used to practice aspects of an embodiment.

The disclosed embodiments may also include software and computer programs (i.e. computer readable program code) embodied on a computer readable medium that incorporate the process steps and instructions described above. The software and computer programs may be provided as a computer program product separately from the mechanical system described herein or the computer program product may be provided as part of the system in, for example a control module of the system. FIG. 8 is a block diagram of one embodiment of a typical apparatus incorporating aspects of the exemplary embodiments that may be used to practice aspects of the exemplary embodiments. As shown, a computer system 50 may be linked to the system 10 of FIG. 1, such that the computer 50 and system 10 are capable of sending information to each other and receiving information from each other. In one embodiment, the computer system 50 could include a server computer adapted to communicate with a network 54, such as for example, the Internet. Computer system 50 and system 10 can be linked together in any conventional manner including a modem, hard wire connection, or fiber optic link. Generally, information can be made available to both computer system 50 and system 10 using a communication protocol typically sent over a communication channel or through a dial-up connection on ISDN line. Computer 50 and system 10 are generally adapted to utilize program storage devices embodying machine readable program source code which is adapted to cause the computer 50 and system 10 to perform the disclosed methods. The program storage devices incorporating aspects of the exemplary embodiments may be devised, made and used as a component of a machine utilizing optics, magnetic properties and/or electronics to perform the procedures and methods disclosed herein. In alternate embodiments, the program storage devices may include magnetic media such as a diskette or computer hard drive, which is readable and executable by a computer. In other alternate embodiments, the program storage devices could include optical disks, read-only-memory ("ROM") floppy disks and semiconductor materials and chips.

Computer system 50 and system 10 may also include a microprocessor for executing stored programs. Computer 50 may include a data storage device 56 on its program storage device for the storage of information and data. The computer program or software incorporating the processes and method steps incorporating aspects of the exemplary embodiments may be stored in one or more computers 50 on an otherwise conventional program storage device. In one embodiment, computer 50 may include a user interface 57, and a display interface 58 from which aspects of the exemplary embodiments can be accessed. The user interface 57 and the display interface 58 can be adapted to allow the input of queries and commands to the system, as well as present the results of the commands and queries.

The system is adapted to be a manually operated device or fully automated system that very rapidly, and continuously, conducts a variety of analyses on electroactive elements in aqueous solutions. The system is designed to operate in a stand alone mode or integrated into a treatment system as an on-line continuous monitoring device. When integrated into a treatment system, this device (along with multiple others integrated into the same system) monitors and controls many control variables while maintaining alarm conditions and affecting immediate control on hydraulic valves and treatment systems. Organic and inorganic elements, ions and compounds can be detected and measured by voltammetric and/or potentiometric method. The concentration range of the measurements will be from 5 parts per trillion (ppt) to grams per liter (parts per thousand), and will range from instantaneous measurement times to less than 5 to 10 minutes.

The system and methods disclosed herein generally provide an improved system for automatically sensing water characteristics, using Stripping Voltammetry and Potentiometric Analysis, in connection with the detection, managing, and processing of fluid material.

The system is adapted to detect electrochemically active components in process streams by sensing using Stripping Voltammetry and Potentiometric Analysis. The 5V technique has a detection limit of 5 parts per trillion for trace contaminants. In an automated or computerized system, data related to the measurement and analysis can be communicated to a central controller, archived and analyzed in accordance with a predefined lookup table. In a treatment system the data can be fed to affect the application of treatment materials to the water treatment mechanism. The same stream can be again sensed after the treatment process using Stripping Voltammetry and Potentiometric Analysis, communicated to a central controller, achieved and analyzed that data in accordance with a predefined lookup table. Data can be fed backward to affect the application of treatment materials to the water treatment mechanism, and affect a series of electrical and mechanical actions in the treatment process if analysis results are out of predefined limits. Therefore, the embodiments described herein can be a system of systems and apply state of the art feed forward and feed back algorithms required for control of modern treatment systems.

It should be understood that the foregoing description is only illustrative of the embodiments. Various alternatives and modifications can be devised by those skilled in the art without departing from the embodiments. Accordingly, the present embodiments are intended to embrace all such alternatives, modifications and variances that fall within the scope of the appended claims.

The invention claimed is:

1. A method for detecting and identifying concentration levels of metal, metalloid, or non-metal ions comprising:
   measuring environmental metrics of a liquid sample;
   preparing and isolating contaminants of concern in a flow of a liquid sample into metal, metalloid, or non-metal ionic forms;
   identifying and determining a concentration of metal, metalloid, or non-metal ionic species through stripping voltammetry; and
   comparing a value of a stripping signal of the sample with a predetermined value to determine if dilution of the sample is required;
   wherein identifying and determining a concentration of metal, metalloid, or non-metal ionic species through, stripping voltammetry includes a quiet time of about 10 sec and changing a deposition potential from about −2.5V to about +2V, changing an initial potential from about −2.5V to about +2V, changing a final potential from about −2.5V to about +2.0V, changing a time of deposition, changing a linear scan rate from about 0.05V/sec to about 1V per second, changing a type of linear scan, and changing a number of cleaning scans from about 1 to about 50.

2. The method of claim 1, wherein identifying and determining a concentration of metal, metalloid, or non-metal ionic species through stripping voltammetry comprises passing the liquid sample through at least one flow through cell containing a working electrode, a reference electrode and an auxiliary electrode.

3. The method of claim 2, wherein the working electrode is located between the auxiliary and reference electrode so that the liquid sample flows on the working electrode before the reference electrode.

4. The method of claim 1, further comprising automatically diluting the sample if the value of the stripping signal is larger than the predetermined value.

5. The method of claim 4, further comprising adjusting fluidic connections so that a sample pump is used for pumping a diluting electrolyte and a reagent pump is substituted as the sample pump.

6. The method of claim 1 wherein identifying and determining a concentration of metal, metalloid, or non-metal ionic species through stripping voltammetry comprises flowing a sample to be analyzed on a working electrode before a reference electrode.

7. The method of claim 1, further comprising automatically redirecting treatment effluent into holding tanks in case of a system malfunction and to automatically notify an operator of alarm conditions.

8. The method of claim 1, further comprising measuring a derivative of oxidation current to determine the concentration of analyte in the sample.

9. The method of claim 1, further comprising measuring a derivative of reduction current to determine the concentration of analyte in the sample.

10. The method of claim 1, further comprising preparing the sample by electrically stimulating the sample by adding reagents and applying electrical current to initiate reactions to expand a range of detection to parts per trillion.

11. The method of claim 1, further comprising measuring derivatives of electrical potential over time as a signal to determine the concentration of contaminants.

12. The method of claim 1, further comprising generating a votlammogram of a signal of the sample and a voltammogram of a signal of the sample with standard addition.

* * * * *

UNITED STATES PATENT AND TRADEMARK OFFICE
CERTIFICATE OF CORRECTION

| | |
|---|---|
| PATENT NO. | : 7,897,032 B2 |
| APPLICATION NO. | : 11/754620 |
| DATED | : March 1, 2011 |
| INVENTOR(S) | : Viltchinskaia et al. |

It is certified that error appears in the above-identified patent and that said Letters Patent is hereby corrected as shown below:

Column 24, line 64, delete "votlammogram" and insert --voltammogram-- therefore.

Signed and Sealed this
Seventeenth Day of May, 2011

David J. Kappos
*Director of the United States Patent and Trademark Office*